United States Patent
Murray et al.

(10) Patent No.: US 11,801,108 B2
(45) Date of Patent: *Oct. 31, 2023

(54) METHODS OF ASSEMBLING A MANIFOLD FOR A MEDICAL WASTE COLLECTION SYSTEM

(71) Applicant: Stryker Corporation, Kalamazoo, MI (US)

(72) Inventors: Sean A Murray, Powell, MI (US); David Hershberger, Kalamazoo, MI (US); Brent S. Lalomia, Portage, MI (US); Stephen Reasoner, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/198,929

(22) Filed: May 18, 2023

(65) Prior Publication Data

US 2023/0285103 A1 Sep. 14, 2023

Related U.S. Application Data

(60) Continuation of application No. 17/325,722, filed on May 20, 2021, now Pat. No. 11,684,442, which is a
(Continued)

(51) Int. Cl.
*A61M 1/00* (2006.01)
*A61B 50/10* (2016.01)
(Continued)

(52) U.S. Cl.
CPC .............. *A61B 50/10* (2016.02); *A61B 50/13* (2016.02); *A61B 50/36* (2016.02); *A61M 1/60* (2021.05);
(Continued)

(58) Field of Classification Search
CPC . A61B 18/148; A61B 2050/185; A61B 50/10; A61B 50/13; A61B 50/36;
(Continued)

(56) References Cited

U.S. PATENT DOCUMENTS 2,784,717 A 3/1957 Thompson
2,854,027 A 9/1958 Kaiser et al.
(Continued)

FOREIGN PATENT DOCUMENTS

CH 391963 A 5/1965
EP 0184629 A2 6/1986
(Continued)

OTHER PUBLICATIONS

ASTM, "Designation: F 960-86, Standard Spefication for Medical and Surgical Suction and Drainage Systems", 2000, 8 pages.
(Continued)

*Primary Examiner* — Dirk R Bass
(74) *Attorney, Agent, or Firm* — Howard & Howard Attorneys PLLC

(57) ABSTRACT

Methods of assembling a manifold for a medical waste collection system. A flapper valve unit is secured to a head of a cap. A filter element is positioned within a shell. Basket hands of the filter element are fitted between first pairs of ribs of the cap skirt. Fingers of the shell are fitted between second pairs of ribs of the cap skirt. The cap is secured to the shell to cover an open distal end of the shell. A drip stop is secured to the proximal end base of the shell to seat within the outlet opening. Ears may be fitted through holes defined by the flapper valve unit and cap holes defined by the cap so as to snap lock to the head of the cap. The hub of the flapper valve unit may be compressed with the ears snap locked to the head of the cap.

16 Claims, 15 Drawing Sheets

Related U.S. Application Data continuation of application No. 16/415,661, filed on May 17, 2019, now Pat. No. 11,045,590, which is a continuation of application No. 15/981,286, filed on May 16, 2018, now abandoned, which is a continuation of application No. 15/722,527, filed on Oct. 2, 2017, now Pat. No. 10,722,617, which is a continuation of application No. 15/334,720, filed on Oct. 26, 2016, now abandoned, which is a division of application No. 14/573,331, filed on Dec. 17, 2014, now Pat. No. 9,782,524, which is a division of application No. 13/957,879, filed on Aug. 2, 2013, now Pat. No. 8,915,897, which is a division of application No. 13/483,084, filed on May 30, 2012, now Pat. No. 8,518,002, which is a division of application No. 12/573,272, filed on Oct. 5, 2009, now Pat. No. 8,216,199, which is a division of application No. 11/554,616, filed on Oct. 31, 2006, now Pat. No. 7,615,037.

(60) Provisional application No. 60/750,862, filed on Dec. 14, 2005.

(51) Int. Cl.
*A61B 50/13* (2016.01)
*A61B 50/36* (2016.01)
*A61B 50/18* (2016.01)
*A61B 18/14* (2006.01)

(52) U.S. Cl.
CPC .............. *A61M 1/63* (2021.05); *A61M 1/631* (2021.05); *A61M 1/71* (2021.05); *A61M 1/732* (2021.05); *A61M 1/74* (2021.05); *A61M 1/742* (2021.05); *A61M 1/743* (2021.05); *A61M 1/77* (2021.05); *A61M 1/78* (2021.05); *A61M 1/782* (2021.05); *A61M 1/784* (2021.05); *A61M 1/79* (2021.05); *A61M 1/84* (2021.05); *A61M 1/92* (2021.05); *A61B 18/148* (2013.01); *A61B 50/362* (2016.02); *A61B 2050/185* (2016.02); *A61M 1/76* (2021.05); *A61M 2205/125* (2013.01); *A61M 2205/3331* (2013.01); *A61M 2205/7545* (2013.01); *A61M 2205/7563* (2013.01); *Y10T 137/87571* (2015.04); *Y10T 137/87676* (2015.04); *Y10T 137/87965* (2015.04)

(58) Field of Classification Search
CPC . A61B 50/362; A61M 1/0001; A61M 1/0005; A61M 1/0007; A61M 1/0023; A61M 1/0027; A61M 1/0031; A61M 1/0033; A61M 1/0035; A61M 1/0049; A61M 1/005; A61M 1/0052; A61M 1/0056; A61M 1/0058; A61M 2205/125; A61M 2205/3331; A61M 2205/7545; A61M 2205/7563; Y10T 137/87571; Y10T 137/87676; Y10T 137/87965
See application file for complete search history.

(56) References Cited

U.S. PATENT DOCUMENTS

| | | |
|---|---|---|
| 3,044,491 A | 7/1962 | Sangster |
| 3,085,689 A | 4/1963 | Hering et al. |
| 3,415,086 A | 12/1968 | Trainer |
| 3,540,062 A | 11/1970 | Leone |
| 3,612,089 A | 10/1971 | Beguiristain |
| 3,936,031 A | 2/1976 | Berman et al. |
| 4,014,329 A | 3/1977 | Welch et al. |
| 4,063,556 A | 12/1977 | Thomas et al. |
| 4,291,706 A | 9/1981 | Voges et al. |
| 4,475,904 A | 10/1984 | Wang |
| 4,653,493 A | 3/1987 | Hoppough |
| 4,658,707 A | 4/1987 | Hawkins et al. |
| 4,728,006 A | 3/1988 | Drobish et al. |
| 4,735,610 A | 4/1988 | Akkas et al. |
| 4,737,148 A | 4/1988 | Blake |
| 4,744,785 A | 5/1988 | Rosenthal et al. |
| 4,857,063 A | 8/1989 | Glenn |
| 4,863,446 A | 9/1989 | Parker |
| 4,915,688 A | 4/1990 | Bischof et al. |
| 4,941,975 A | 7/1990 | Schewe |
| 4,990,137 A | 2/1991 | Graham |
| 5,074,334 A | 12/1991 | Onodera |
| 5,112,019 A | 5/1992 | Metzler et al. |
| 5,115,842 A | 5/1992 | Crafts et al. |
| 5,182,542 A | 1/1993 | Adelman et al. |
| 5,195,961 A | 3/1993 | Takahashi et al. |
| 5,201,417 A | 4/1993 | Outlaw, III |
| 5,242,434 A | 9/1993 | Terry |
| 5,242,474 A | 9/1993 | Herbst et al. |
| 5,284,621 A | 2/1994 | Kaufman |
| 5,308,583 A | 5/1994 | Sanuki |
| 5,312,377 A | 5/1994 | Dalton |
| 5,312,479 A | 5/1994 | Weinstein et al. |
| 5,419,687 A | 5/1995 | Adahan |
| 5,458,138 A | 10/1995 | Gajo |
| 5,464,042 A | 11/1995 | Taunhorst |
| 5,476,447 A | 12/1995 | Noda et al. |
| 5,601,712 A | 2/1997 | Adams et al. |
| 5,613,966 A | 3/1997 | Makower et al. |
| 5,624,417 A | 4/1997 | Cook et al. |
| 5,637,103 A | 6/1997 | Kerwin et al. |
| 5,639,064 A | 6/1997 | deCler et al. |
| 5,725,516 A | 3/1998 | Cook et al. |
| 5,736,098 A | 4/1998 | Kerwin et al. |
| 5,792,126 A | 8/1998 | Tribastone et al. |
| 5,807,359 A | 9/1998 | Bemis et al. |
| 5,817,068 A | 10/1998 | Urrutia |
| 5,830,199 A | 11/1998 | Chaffringeon |
| 5,863,443 A | 1/1999 | Mainwaring |
| 5,871,476 A | 2/1999 | Hand |
| 5,885,240 A | 3/1999 | Bradbury et al. |
| 5,901,717 A | 5/1999 | Dunn et al. |
| 5,911,786 A | 6/1999 | Nielsen et al. |
| 5,914,047 A | 6/1999 | Griffiths |
| 5,922,196 A | 7/1999 | Baumann |
| 5,947,954 A | 9/1999 | Bonaldo |
| 5,968,032 A | 10/1999 | Sleister |
| 5,997,733 A | 12/1999 | Wilbur et al. |
| 6,024,720 A | 2/2000 | Chandler et al. |
| 6,027,490 A | 2/2000 | Radford et al. |
| 6,045,596 A | 4/2000 | Holland, Jr. et al. |
| 6,056,731 A | 5/2000 | Koetke et al. |
| 6,058,731 A | 5/2000 | Byczynski et al. |
| 6,070,751 A | 6/2000 | Mejias |
| 6,180,000 B1 | 1/2001 | Wilbur et al. |
| 6,187,188 B1 | 2/2001 | Janik et al. |
| 6,222,283 B1 | 4/2001 | Regla |
| 6,244,311 B1 | 6/2001 | Hand et al. |
| 6,273,296 B1 | 8/2001 | Brown |
| 6,331,246 B1 | 12/2001 | Beckham et al. |
| 6,391,102 B1 | 5/2002 | Bodden et al. |
| 6,400,141 B1 | 6/2002 | Apel et al. |
| 6,488,675 B1 | 12/2002 | Radford et al. |
| 6,506,168 B1 | 1/2003 | Fathallah et al. |
| 6,579,455 B1 | 6/2003 | Muzik et al. |
| 6,673,055 B2 | 1/2004 | Bemis et al. |
| 6,695,891 B2 | 2/2004 | Reid |
| 6,770,061 B2 | 8/2004 | Wildman |
| 6,788,211 B2 | 9/2004 | Kouznetsov et al. |
| 6,837,267 B2 | 1/2005 | Weis et al. |
| 6,875,193 B1 | 4/2005 | Bonnette et al. |
| 6,893,056 B2 | 5/2005 | Guala |
| 6,893,425 B2 | 5/2005 | Dunn et al. |
| 6,918,893 B2 | 7/2005 | Houde et al. |
| 6,935,459 B2 | 8/2005 | Austin et al. |
| 6,951,228 B2 | 10/2005 | Steigerwalt et al. |

(56) References Cited

U.S. PATENT DOCUMENTS

| | | |
|---|---|---|
| 7,090,663 B2 | 8/2006 | Dunn et al. |
| 7,153,294 B1 | 12/2006 | Farrow |
| 7,258,711 B2 | 8/2007 | Dunn et al. |
| 7,459,078 B2 | 12/2008 | Klein et al. |
| 7,615,037 B2 | 11/2009 | Murray et al. |
| 7,621,898 B2 | 11/2009 | Alomia et al. |
| 8,216,199 B2 | 7/2012 | Murray et al. |
| 8,509,736 B2 | 8/2013 | Hodge |
| 8,518,002 B2 | 8/2013 | Murray et al. |
| RE44,920 E | 6/2014 | Dunn et al. |
| 8,740,866 B2 | 6/2014 | Reasoner et al. |
| 8,915,897 B2 | 12/2014 | Murray et al. |
| 9,143,610 B2 | 9/2015 | Hodge |
| 9,579,428 B1 | 2/2017 | Reasoner et al. |
| 9,782,524 B2 | 10/2017 | Reasoner et al. |
| 10,722,617 B2 | 7/2020 | Murray et al. |
| 11,045,590 B2 | 6/2021 | Murray et al. |
| 2001/0040123 A1 | 11/2001 | Beckham |
| 2002/0026160 A1 | 2/2002 | Takahashi et al. |
| 2003/0164600 A1 | 9/2003 | Dunn et al. |
| 2003/0213733 A1 | 11/2003 | Beckham et al. |
| 2004/0016691 A1 | 1/2004 | Smit et al. |
| 2004/0079418 A1 | 4/2004 | Weis et al. |
| 2004/0102743 A1 | 5/2004 | Walker |
| 2004/0138632 A1 | 7/2004 | Bemis et al. |
| 2004/0143227 A1 | 7/2004 | Rollin et al. |
| 2004/0163884 A1 | 8/2004 | Austin et al. |
| 2004/0261525 A1 | 12/2004 | Chen |
| 2005/0004537 A1 | 1/2005 | Dunn et al. |
| 2005/0010179 A1 | 1/2005 | Dunn et al. |
| 2005/0127212 A1 | 6/2005 | Kassanits |
| 2005/0139532 A1 | 6/2005 | Hershberger et al. |
| 2005/0171495 A1 | 8/2005 | Austin et al. |
| 2005/0173638 A1 | 8/2005 | Powell |
| 2005/0183780 A1 | 8/2005 | Michaels et al. |
| 2005/0187529 A1 | 8/2005 | Reasoner et al. |
| 2005/0189288 A1 | 9/2005 | Hershberger et al. |
| 2005/0209585 A1 | 9/2005 | Nord et al. |
| 2007/0135778 A1 | 6/2007 | Murray et al. |
| 2007/0135779 A1 | 6/2007 | Alomia et al. |
| 2010/0030132 A1 | 2/2010 | Niezgoda et al. |
| 2014/0338529 A1 | 11/2014 | Reasoner et al. |
| 2017/0043064 A1 | 2/2017 | Reasoner et al. |
| 2018/0221804 A1 | 8/2018 | Reasoner et al. |
| 2018/0243487 A1 | 8/2018 | Murray et al. |
| 2018/0256790 A1 | 9/2018 | Murray et al. |
| 2019/0269833 A1 | 9/2019 | Murray et al. |
| 2021/0268165 A1 | 9/2021 | Murray et al. |

FOREIGN PATENT DOCUMENTS

| | | |
|---|---|---|
| EP | 0691279 A2 | 1/1996 |
| EP | 0843122 A2 | 5/1998 |
| EP | 0882440 A2 | 12/1998 |
| EP | 1166805 A2 | 1/2002 |
| EP | 1099854 B1 | 5/2002 |
| EP | 1380316 A1 | 1/2004 |
| EP | 1380316 B1 | 10/2007 |
| EP | 2359878 A2 | 8/2011 |
| EP | 2359879 A2 | 8/2011 |
| EP | 2364736 A2 | 9/2011 |
| EP | 2384776 A1 | 11/2011 |
| EP | 2384777 A1 | 11/2011 |
| EP | 2388024 A1 | 11/2011 |
| EP | 2388025 A1 | 11/2011 |
| FR | 2744359 A1 | 8/1997 |
| GB | 2058227 A | 4/1981 |
| JP | H02145393 U | 12/1990 |
| JP | H06178780 A | 6/1994 |
| JP | H08500763 A | 1/1996 |
| JP | H10501145 A | 2/1998 |
| JP | H10503391 A | 3/1998 |
| JP | H11000392 A | 1/1999 |
| JP | 2001017489 A | 1/2001 |
| JP | 2003325658 A | 11/2003 |
| JP | 2003534088 A | 11/2003 |
| WO | 9308897 A1 | 5/1993 |
| WO | 1993008897 A1 | 5/1993 |
| WO | 9626750 A1 | 9/1996 |
| WO | 9900154 A1 | 1/1999 |
| WO | 03075821 A2 | 9/2003 |
| WO | 2005042061 A1 | 5/2005 |
| WO | 2005079947 A2 | 9/2005 |
| WO | 2007070570 A2 | 6/2007 |
| WO | 2007079319 A2 | 7/2007 |
| WO | 2007103842 A2 | 9/2007 |

OTHER PUBLICATIONS

English language abstract for JP 2003-534088 extracted from espacenet.com database on Feb. 26, 2018, 2 pages.
English language abstract and machine-assisted English translation for EP 1 380 316 extracted from espacenet.com database on Feb. 26, 2018, 21 pages.
English language abstract and machine-assisted English translation for FR 2 744 359 extracted from espacenet.com database on Feb. 26, 2018, 6 pages.
English language abstract and machine-assisted English translation for JP 2001-017489 extracted from espacenet.com database on Feb. 26, 2018, 27 pages.
English language abstract and machine-assisted English translation for JP 2003-325658 extracted from espacenet.com database on Feb. 26, 2018, 20 pages.
English language abstract and machine-assisted English translation for JPH 02-145393 extracted from PAJ database on Feb. 26, 2018, 2 pages.
English language abstract and machine-assisted English translation for JPH 06-178780 extracted from espacenet.com database on Feb. 26, 2018, 28 pages.
English language abstract for EP 0 882 440 extracted from espacenet.com database on Feb. 26, 2018, 1 page.
English language abstract for JPH 08-500763 extracted from espacenet.com database on Feb. 26, 2018, 2 pages.
English language abstract for JPH 10-501145 extracted from espacenet.com database on Feb. 26, 2018, 1 page.
English language abstract for JPH 10-503391 extracted from espacenet.com database on Feb. 26, 2018, 2 pages.
English language abstract for JPH 11392 extracted from espacenet.com database on Feb. 26, 2018, 1 page.
EP Search Report, Application No. 11 002 751.3, dated Feb. 27, 2012.
EP Search Report, Application No. 11 002 752.1, dated Feb. 27, 2012.
EP Search Report, Application No. 11 002 753.9, dated Feb. 27, 2012.
European Patent Office, "Examination Report for EP App. No. 06 849 075.4", dated Oct. 2011.
International Search Report and Written Opinion, for PCT/US2006/047531, dated Aug. 23, 2007.
International Search Report dated May 31, 2007; International Application No. PCT/US2006/047531 filed Dec. 13, 2006 and Written Opinion.
International Search Report for Application No. PCT/US2007/063253 dated Dec. 5, 2007, 5 pages.
International Search Report for PCT/US2006/047531 dated May 31, 2007.
International Search Report for PCT/US2006/061791 dated Jan. 23, 2008.
Invitation to Pay Additional Fees and Communication Relating to the Results of the Partial International Search for PCT/US2006/061791 dated Sep. 9, 2007, 3 pages.
ISA Search Report and Written Opinion for PCT/US2006/061791, dated Jun. 2008.
LMS, "Medi-Flo Valves Specification Sheets", Nov. 2005, 7 pages.
LMS, "V33 SureFlo Valve", 2005, 1 page.
Machine-assisted English translation for CH 391963 extracted from espacenet.com database on Feb. 26, 2018, 11 pages.

(56) References Cited

OTHER PUBLICATIONS

PCT/US2006/061791 International Search Report and Written Opinion, dated Jan. 1, 2008.
Portable Suction Sources, Health Devices, vol. 7, No. 5, Mar. 1978, pp. 119-141.
Search Report for EP Publication No. 2388024A1, dated Oct. 20, 2011.
*Stryker Corporation et al.* v. *Poseidon Surgical, LLC*, "Defendants/Counterclaimants Initial Invalidity and Unenforceability Contentions", United States District Court, Western District of Michigan, Southern Division, Civil Action No. 1:16-cv-01199, Mar. 29, 2017, 40 pages.
Stryker Instruments, "Neptune Waste Management System, Instructions for Use, Neptune Gold Rover, REF 700-2, Neptune Docking Station, REF 700-6", Sep. 2005, 19 pages.
The Merriam-Webster Dictionary, "Definition of Disk or Disc", Eleventh Edition, p. 206, 2 pages.
USPTO "Office Action" dated Feb. 2009 from U.S. Appl. No. 11/554,616.
USPTO "Office Action" dated Sep. 2008 from U.S. Appl. No. 11/554,616.
USPTO Office Action, dated Jan. 2009 from U.S. Appl. No. 11/610,071.
Vernay Laboratories, "Valve Specification Sheets", Nov. 2005, 6 pages.
*Zimmer Surgical, Inc. and Dornoch Medical Systems*, Inc. v. *Stryker Corporation and Stryer Sales Corporation* v. *Zimmer, Inc., Zimmer Surgical, Inc., Dornoch Medical Systems, Inc. and Zimmer U.S., Inc.*, "Counterclaim Defendants' First Supplemental Invalidity Contentions dated May 15, 2018", In the United States District Court for the District of Delaware, Case No. 16-679-RGA-MPT, 4 pages.
*Zimmer Surgical, Inc. and Dornoch Medical Systems, Inc.* v. *Stryker Corporation and Stryer Sales Corporation v. Zimmer, Inc., Zimmer Surgical, Inc., Dornoch Medical Systems, Inc. and Zimmer U.S., Inc.*, "Counterclaim Defendants' Second Supplemental Invalidity Contentions dated May 29, 2018", In the United States District Court for the District of Delaware, Case No. 16-679-RGA-MPT, 94 pages.
*Zimmer Surgical, Inc. and Dornoch Medical Systems, Inc.* v. *Stryker Corporation and Stryker Sales Corporation, and Stryker Corporation and Stryker Sales Corporation* v. *Zimmer Surgical, Inc., Zimmer, Inc. and Dornoch Medical Systems, Inc.*, "Memorandum Opinion filed Jun. 19, 2018", In the United States District Court for the District of Delaware, Case No. 16-679-RGA, 24 pages.
*Zimmer Surgical, Inc. and Dornoch Medical Systems, Inc.* v. *Stryker Corporation and Stryker Sales Corporation, and Stryker Corporation and Stryker Sales Corporation* v. *Zimmer Surgical, Inc., Zimmer, Inc. and Dornoch Medical Systems, Inc.*, "Stryker's Opening Claim Construction Brief for U.S. Pat. No. 9,579,428 filed Feb. 2, 2018", In the United States District Court for the District of Delaware, Case No. 16-679-RGA, 25 pages.
*Zimmer Surgical, Inc. and Dornoch Medical Systems, Inc.* v. *Stryker Corporation and Stryker Sales Corporation, and Stryker Corporation and Stryker Sales Corporation* v. *Zimmer Surgical, Inc., Zimmer, Inc. and Dornoch Medical Systems, Inc.*, "Stryker's Reply Claim Construction Brief for U.S. Pat. No. 9,579,428 filed Mar. 20, 2018", In the United States District Court for the District of Delaware, Case No. 16-679-RGA, 25 pages.
*Zimmer Surgical, Inc. and Dornoch Medical Systems, Inc.* v. *Stryker Corporation and Stryker Sales Corporation, and Stryker Corporation and Stryker Sales Corporation* v. *Zimmer Surgical, Inc., Zimmer, Inc. and Dornoch Medical Systems, Inc.*, "Supplemental Joint Claim Construction Chart for U.S. Pat. No. 9,579,428 filed Dec. 20, 2017", In the United States District Court for the District of Delaware, Case No. 16-679-RGA, 11 pages.
*Zimmer Surgical, Inc. and Dornoch Medical Systems, Inc.* v. *Stryker Corporation and Stryker Sales Corporation, and Stryker Corporation and Stryker Sales Corporation* v. *Zimmer Surgical, Inc., Zimmer, Inc. and Dornoch Medical Systems, Inc.*, "Claim Construction Order filed Jun. 26, 2018", In the United States District Court for the District of Delaware, Case No. 16-679-RGA, 3 pages.
*Zimmer Surgical, Inc et al.* v. *Stryker Corporation et al.* v. *Zimmer, Inc et al.*, "Counterclaim Defendants' Invalidity Contentions", United States District Court, District of Delaware Case No. C.A. No. 16-679-RGA-MPT, Nov. 17, 2017, 51 pages.
*Zimmer Surgical, Inc.* v. *Stryker Corporation*, "Declaration of Neil Sheehan Regarding U.S. Pat. No. 9,579,428 filed Feb. 2, 2018", In the United States District Court for the District of Delaware, Case No. 16-679-RGA, 40 pages.
*Zimmer Surgical, Inc.* v. *Stryker Corporation*, "Declaration of Terry N. Layton filed May 21, 2018", United States Patent and Trademark Office Before the Patent Trial and Appeal Board, Case IPR2018-01089, U.S. Pat. No. 9,579,428, 91 pages.
*Zimmer Surgical, Inc.* v. *Stryker Corporation*, "Patent Owner's Preliminary Response filed Sep. 10, 2018", United States Patent and Trademark Office Before the Patent Trial and Appeal Board, Case IPR2018-01089, U.S. Pat. No. 9,579,428, 74 pages.
*Zimmer Surgical, Inc.* v. *Stryker Corporation*, "Petition for Inter Partes Review of U.S. Pat. No. 9,579,428 filed May 21, 2018", United States Patent and Trademark Office Before the Patent Trial and Appeal Board, Case IPR2018-01089, U.S. Pat. No. 9,579,428, 90 pages.

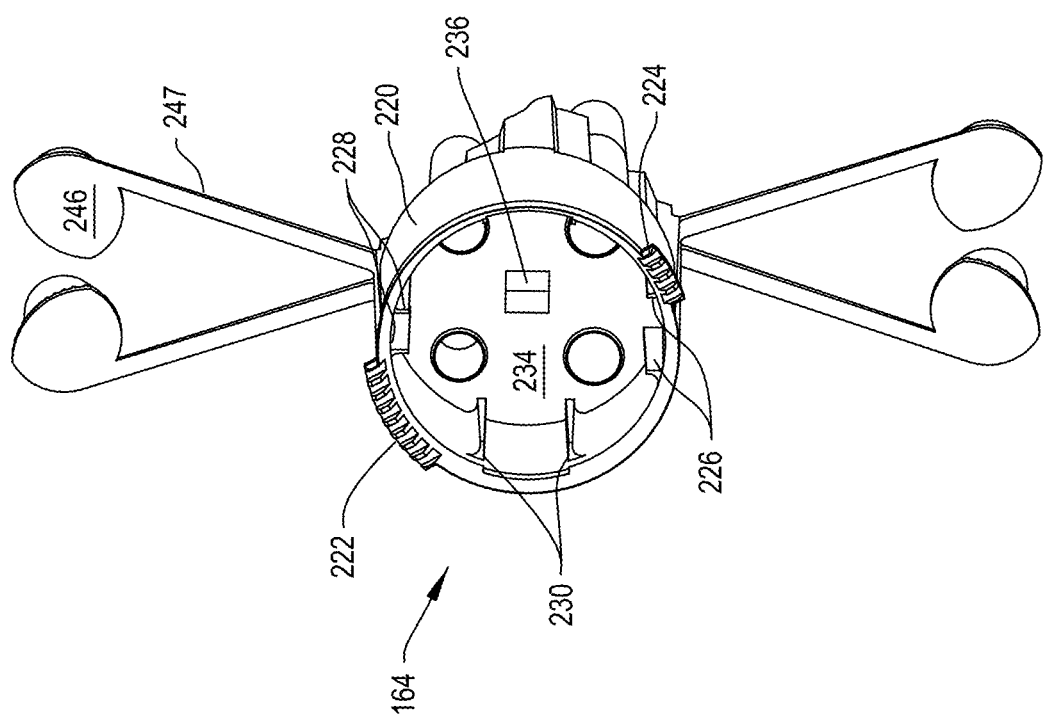

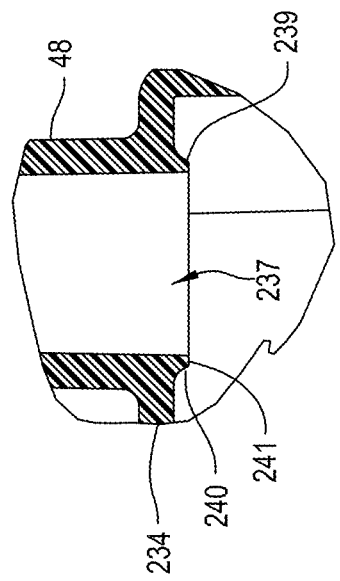
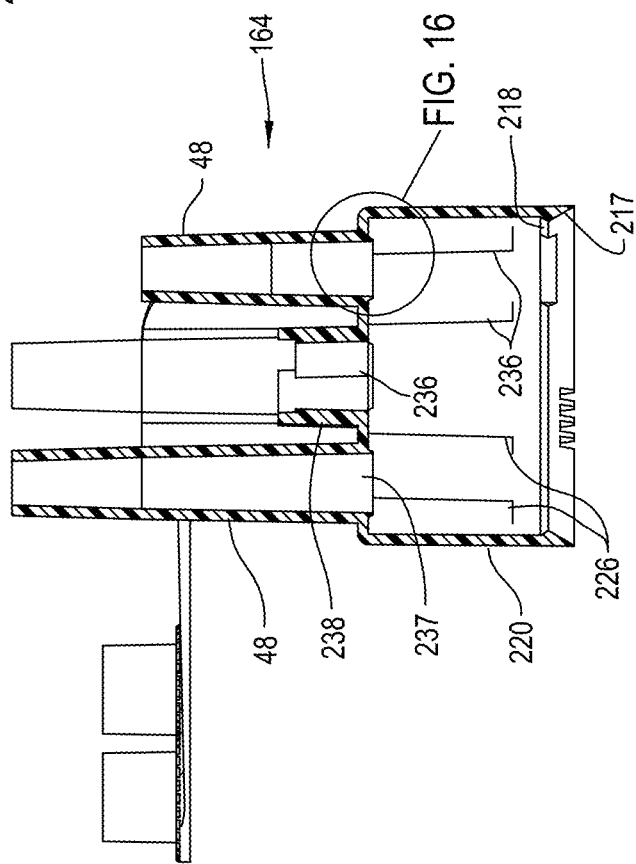

METHODS OF ASSEMBLING A MANIFOLD FOR A MEDICAL WASTE COLLECTION SYSTEM

CROSS REFERENCE TO RELATED APPLICATIONS

This application is a continuation of and claims priority to and through co-pending U.S. patent application Ser. No. 17/325,722, filed May 20, 2021, which is a continuation of U.S. patent application Ser. No. 16/415,661, filed on May 17, 2019, now U.S. Pat. No. 11,045,590 which is a continuation of U.S. patent application Ser. No. 15/981,286, filed on May 16, 2018, now abandoned, which is a continuation of U.S. application Ser. No. 15/722,527, filed on Oct. 2, 2017, now U.S. Pat. No. 10,722,617, which is a continuation of U.S. application Ser. No. 15/344,720, filed on Oct. 26, 2016, now abandoned, which is a divisional of U.S. application Ser. No. 14/573,331, filed on Dec. 17, 2014, now U.S. Pat. No. 9,782,524, which is a divisional of U.S. application Ser. No. 13/957,879, filed on Aug. 2, 2013, now U.S. Pat. No. 8,915,897, which is a divisional of U.S. application Ser. No. 13/483,084, filed on May 30, 2012, now U.S. Pat. No. 8,518,002, which is a divisional of U.S. application Ser. No. 12/573,272, filed on Oct. 5, 2009, now U.S. Pat. No. 8,216,199, which is a divisional of U.S. application Ser. No. 11/554,616, filed on Oct. 31, 2006, now U.S. Pat. No. 7,615,057, which claims priority to U.S. Provisional Patent Application No. 60/750,862, filed on Dec. 14, 2005. The entire contents of the aforementioned applications are incorporated herein by reference.

FIELD OF THE DISCLOSURE

This invention relates generally to a system for collecting waste generated during a surgical procedure. More particularly, this invention relates to a waste collection system with a removable intake manifold that, when removed from the system, prevents the release of uncollected waste still in the manifold or the complementary receiver to which the manifold was attached.

BACKGROUND

A byproduct of the performance of some medical and surgical procedures is the generation of liquid, semi-solid and solid waste. This waste includes body fluids, such as blood, and irrigating solution that are introduced to the body site at which the procedure is performed. Solid and semi-solid waste generated during a procedure includes bits of tissue and small pieces of the surgical material that may be left at the site. Ideally, the waste is collected upon generation so it neither fouls the surgical site nor becomes a biohazard in the operating room or other location at which the procedure is being performed.

A number of systems are available for use by surgical personnel for collecting this waste as it is generated. Generally, these units include a suction source, tubing that extends from the suction source and a containment unit between the tubing and the suction source. When the system is actuated, waste is drawn through the opening end of the tubing. The suction draws the waste through the tubing so that it flows into and is stored in the containment unit.

One such system is Applicants' Assignee's NEPTUNE surgical waste collection system. This particular system includes a mobile unit that includes a suction pump and a canister. Tubing is connected to the canister through a removable manifold. Since this unit is mobile, it can be positioned in relatively close proximity to the patient on which the procedure is being performed. This reduces the extent to which the suction tubing, which invariably also functions as operating room clutter, is present around the surgical personnel. This system also has features that reduce the extent to which the surgical and support personnel are potentially exposed to the materials collected by the system. U.S. patent application Ser. No. 11/060,665, WASTE COLLECTION UNIT, published as U.S. Patent Pub. No. US 2005/0187529 A1 on 25 Aug. 2005, the contents of which are incorporated herein by reference, describes a number of features of this system.

Another feature of this system is the intake manifold. This manifold includes a filter element that traps large bits of solid matter. This is desirable because these solids can potentially clog the down line components of the system. Moreover, the manifold is formed from material that makes it possible to provide the manifold as a single use item. After use of the system, effort does not have to be spent sterilizing the manifold, with its narrow conduits, or its internal filter. Instead, personnel handling the used manifold only need to contact the outer surface of this component. This process further minimizes the extent to which these individuals potentially come into contact with the waste material. The Applicants' Assignee's U.S. patent application Ser. No. 11/060,977, MANIFOLD AND FILTER ASSEMBLY WITH FILTER BASKET, published as U.S. Patent Pub. No. US 2005/0189288 A1 on 1 Sep. 2006, the contents of which are incorporated herein by reference, provided a more detailed description of this type of manifold.

Use of the above system significantly reduces the extent to which medical/surgical personnel are exposed to potentially hazardous medical waste. Nevertheless, there are some disadvantages associated with the known waste collection systems. For example, in the present system, the manifold extends directly into the canister in which the waste is stored. Small droplets of waste can adhere to the sides of the manifold. Upon removal of the manifold from the mobile unit, this adhered liquid is essentially an uncontained waste in the surrounding environment. If the liquid is not immediately wiped off the manifold, it can potentially fall of the manifold and be added waste matter that needs to be cleaned off a floor or other surface.

Also, the filter of the manifold does more than trap the small bits of solid that can clog the downstream components of the mobile unit. The filter also traps an appreciable volume of semi-solid state waste. Thus, care must be taken when removing the manifold to ensure that this waste does not escape.

Moreover, medical personnel sometimes visually monitor the volume of material collected by the mobile unit canister. This monitoring is performed to provide a rough estimate of the volume of fluid withdrawn from the patient during a procedure. If an appreciable amount of liquid remains trapped in the manifold, the accuracy of the quick visual estimate of collected stored fluid can be adversely affected.

Further, upon removal of the manifold from the canister, the port in which the manifold was seated opens to the ambient environment. Material collected in the canister is known to emit smells that are typically considered unpleasant. Thus, the removal of the manifold results in the release of these odors into the environment.

Also, the air and other fluids flowing through the waste collection system, both the manifold and mobile unit, can generate noise. This noise contributes to the unwanted background noise in an operating room.

SUMMARY

This invention is directed to a new and useful system for collecting surgical and medical waste. The system of this invention has an intake manifold to which suction tubes are connected. The manifold is removably coupled to a manifold receiver, also part of the system. The manifold and complementary receiver are designed to minimize the release of uncontained fluids upon removal and replacement of the manifold.

The intake manifold of this invention has a housing. At one end, a number of inlet fittings extend outwardly. These inlet fittings receive suction tubes. The opposed end of the housing has an opening through which a suction is drawn. A drip stop is fitted in this opening. When the manifold is seated in the complementary receiver, the opening seats in a tubular boss that is part of the receiver. A portion of the drip stop is disposed against the outer surface boss so as to prevent leakage of material around the boss.

The drip stop is further formed to have a selectively openable valve that extends into the space defined by the opening. This valve is normally closed. Once the manifold is removed from the receiver, this head closes to prevent waste leakage from the manifold. In one version of the invention flaps form the valve integral with the drip stop. When the manifold is fitted to the receiver, the flaps are the drip stop members that prevent suction loss between the boss and the surrounding manifold.

The receiver boss extends from a valve, also part of the receiver. Normally, this valve closes a fluid conduit that extends into a canister in which the waste is stored. As part of the preparation of the system for operation, the manifold is properly seated in the receiver. The manifold includes a geometric feature that engages a complementary drive member integral with the valve. Thus, the placement of the manifold in the receiver displaces the valve integral with the drip stop into the open state. There is an unrestricted fluid path from the manifold to the complementary conduit that leads to the canister.

When the manifold is removed, the valve returns to the closed state. The return of the valve to this state blocks the release of unpleasant vapors from the canister when no manifold is removed from the system.

Internal to the manifold of this invention is a filter basket. The filter basket both traps large bits of solid matter that are part of the waste stream while allowing substantially the whole of the liquid component of the stream to flow therethrough. Upon completion of the procedure, only a minimal amount of liquid state waste, the type that is the most prone to leakage, is left in the manifold.

BRIEF DESCRIPTION OF THE DRAWINGS

The invention is pointed out with particularity in the claims. The above and further features and advantages of the invention are understood by the following Detailed Description taken in conjunction with the accompanying drawings in which:

FIG. 14 is a perspective view of the inside of the manifold cap;

FIG. 15 is a cross sectional view of the manifold cap;

FIG. 16 is an enlarged cross sectional view of a port formed in the manifold cap wherein a fitting opens into a void space internal to the manifold;

DETAILED DESCRIPTION

I. Overview

Figure 1:
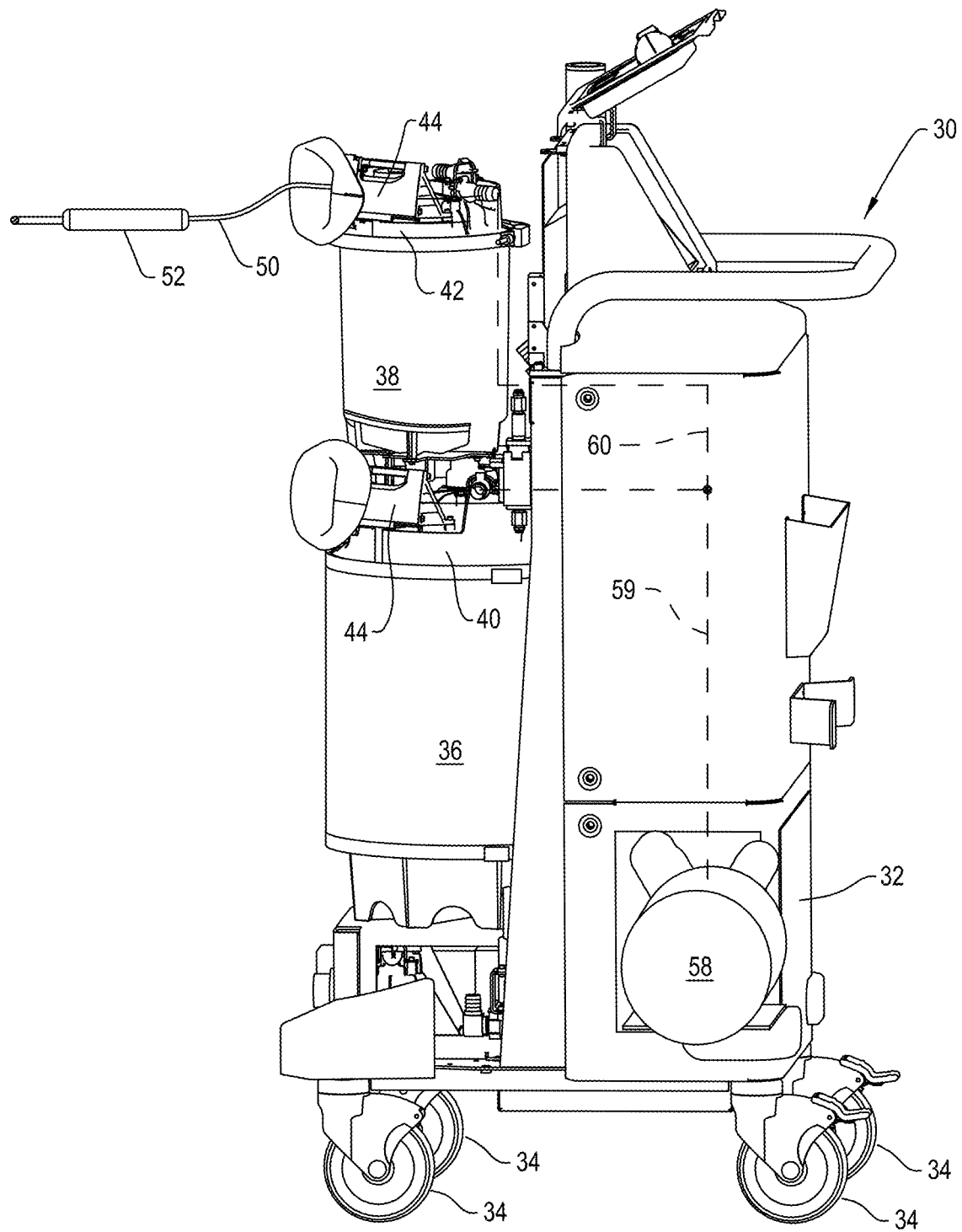
FIG. 1 is a side view of a medical/surgical waste collection system of this invention.

FIG. 1 illustrates a waste collection system 30 constructed in accordance with this invention. The system 30, sometimes referred to as a mobile unit, includes a base 32. The cover and door assemblies that normally conceal the components are mobile unit 30 are not present in FIG. 1 so that these components can be seen. Wheels 34 attached to the bottom of the base 32 provide the system with mobility. Two canisters 36 and 38 are mounted to the base 32. A first one of the canisters, canister 36, has a relatively large interior volume, between approximately 10 and 40 liters. The second canister, canister 38, has a smaller volume, between approximately 1 and 10 liters. Each canister 36 and 38 has a cap 40 and 42, respectively.

Figure 2:
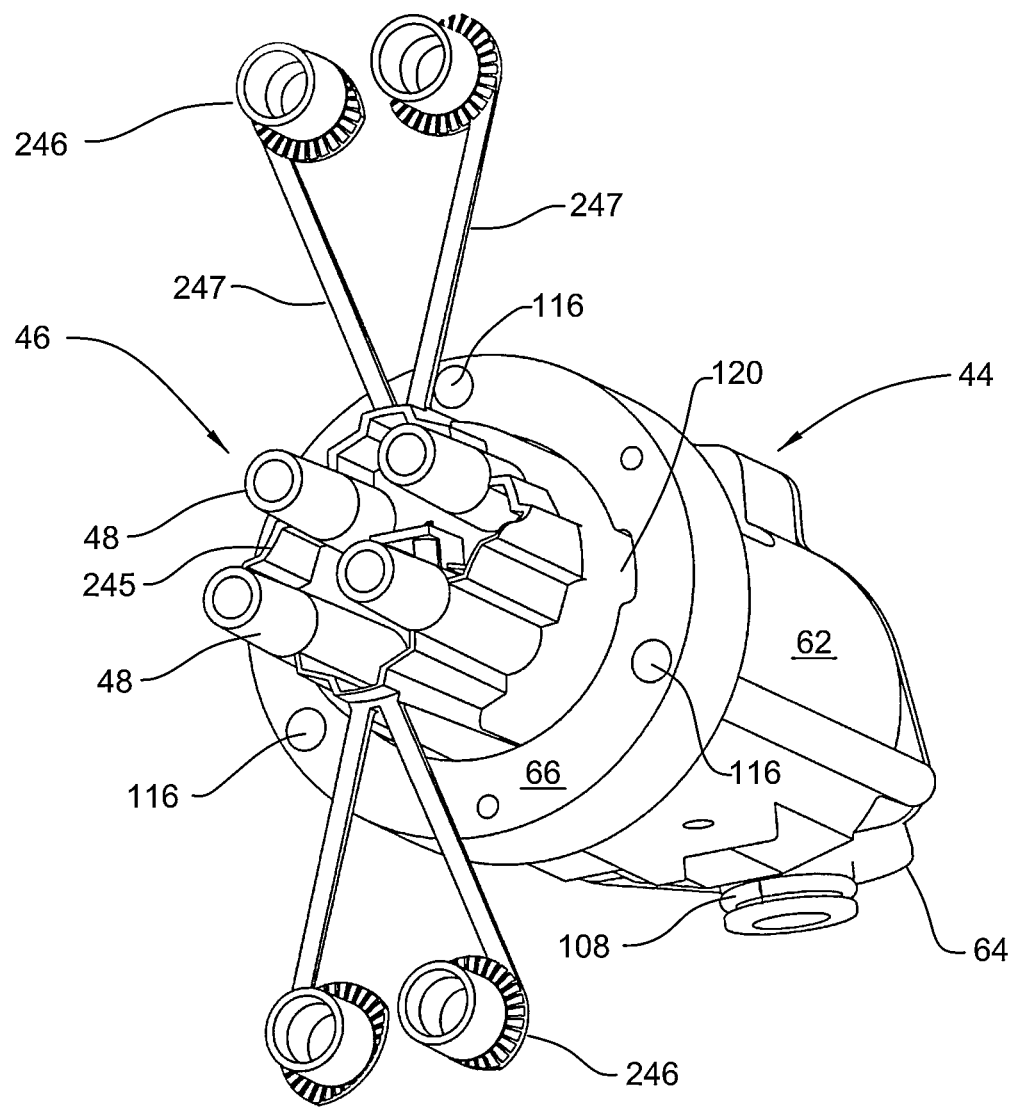
FIG. 2 is a perspective view of the manifold seated in the manifold receiver.
Figure 3:
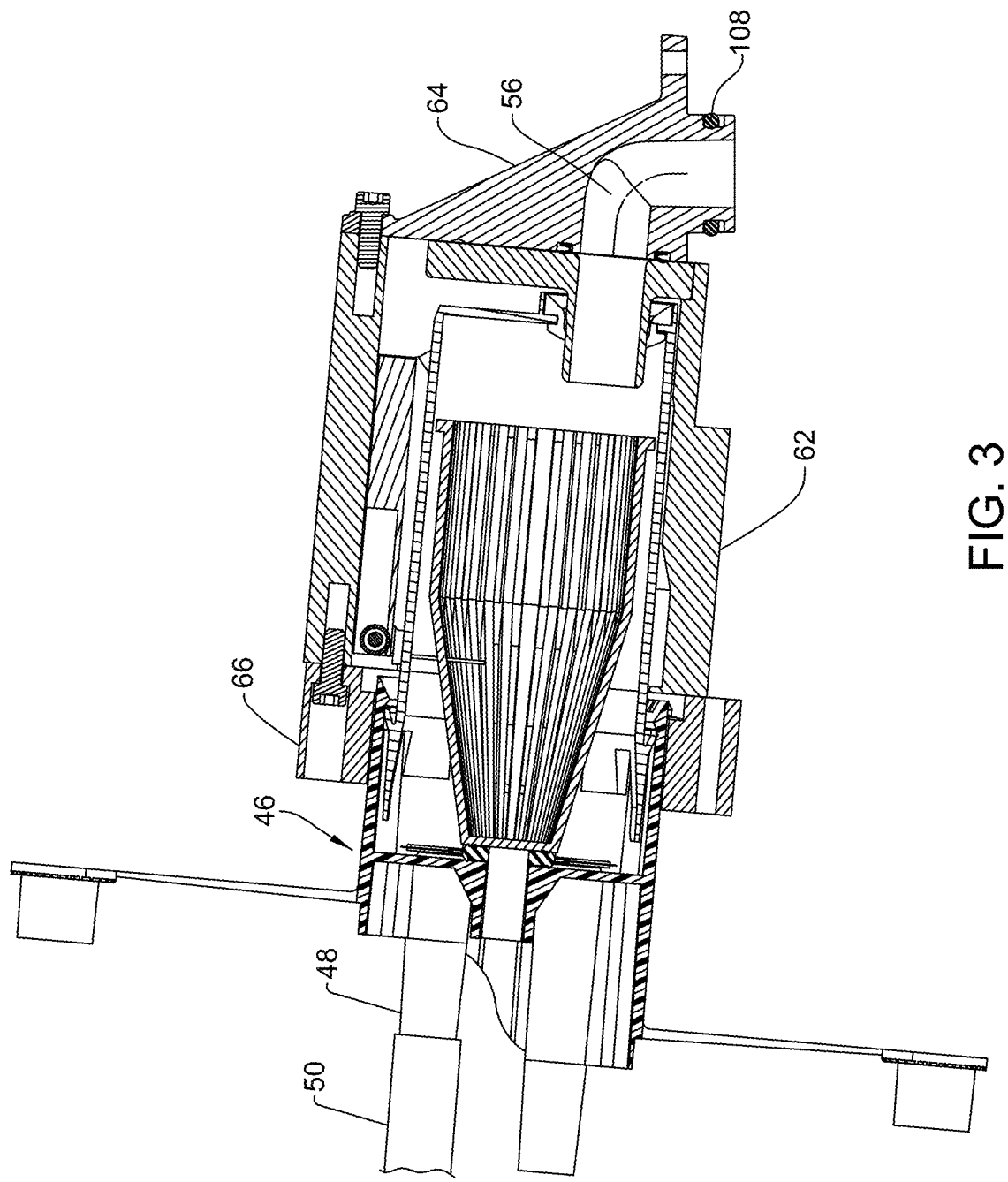
FIG. 3 is a cross sectional view showing the manifold seated in the manifold receiver.

Attached to each canister cap 40 and 42 is a manifold receiver 44. A manifold 46, seen in FIGS. 2 and 3, is removably seated in each manifold receiver 44. As described below, each manifold 46 is formed with a number of fittings 48. Each fitting 48 receives a separate suction line 50, (one shown in FIG. 3). The distal end of each suction line 50 is attached to a suction applicator 52 (FIG. 1). ("Distal," it is understood means towards the surgical site at which the suction is applied. "Proximal" means away from the surgical site.) While in FIG. 1, suction applicator 52 is shown as handpiece specifically and solely designed to apply suction, it should be understood that this is exemplary, not limiting. Sometimes the suction applicator 52 is built into another surgical tool, such as an endoscope or ablation tool, applied to surgical site to accomplish a task other than applying suction.

Internal to each manifold receiver 44 is a conduit 56 (FIG. 3). Conduit 56 functions as a fluid communications path from the manifold 46 into the canister 36 or 38 with which the receiver is associated.

Also part of mobile unit 30 is a suction pump 58. Conduits 59 and 60, (shown as dashed lines in FIG. 1) connect each canister 36 and 38 to the inlet port of the suction pump 58. When suction pump 58 is actuated, the resultant suction draws matter into the suction applicator 52 and through the associated suction line 50, manifold 46 and manifold receiver 44. The waste stream flows from the manifold receiver 44 into the associated canister 36 or 38. Liquid and small solid bits of matter entrained in this flow stream precipitate out of the stream into the canister 36 or 38. This waste is thus stored in the canister 36 or 38 until the canister is emptied. Gas and any small bits of matter entrained in this flow stream flow from the canister towards the suction pump 58. Filters, not illustrated and not part of this invention, trap the viral and bacterial-sized matter and some of the components of the gas in this fluid stream prior to the stream being drawing into and exhausted out of the suction pump 58.

II. Manifold Receiver

Figure 4:
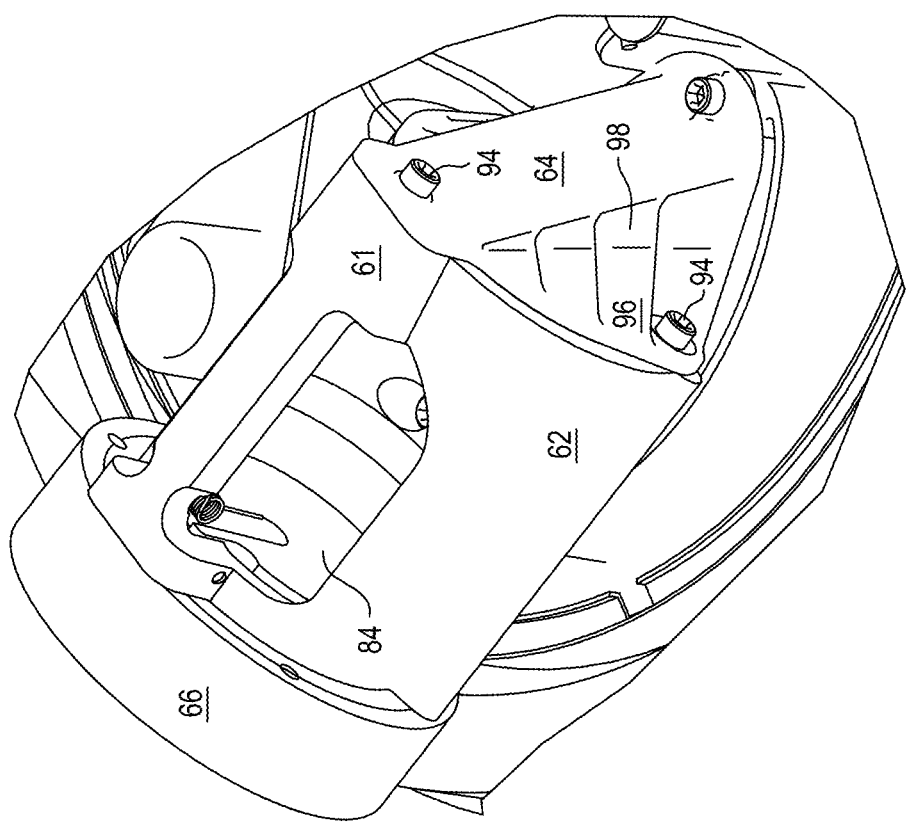
FIG. 4 is a perspective view of a manifold receiver mounted to a canister lid.

As seen in FIGS. 2, 3 and 4, a manifold receiver 44 consists of three primary static components. A housing 62 receives the proximal end of the manifold 46. A receiver adapter 64 holds the manifold receiver housing 62 to the associated canister cap 40 or 42. Adaptor 64 also includes conduit 56 that functions as the flow path from the manifold receiver housing 62 into the associated canister 36 or 38. A lock ring 66 is attached to distal front end of manifold receiver housing 62. Lock ring 66 is formed with geometric features to ensure that, when a manifold 46 is fitted in receiver 44, the manifold is properly aligned.

Figure 5:
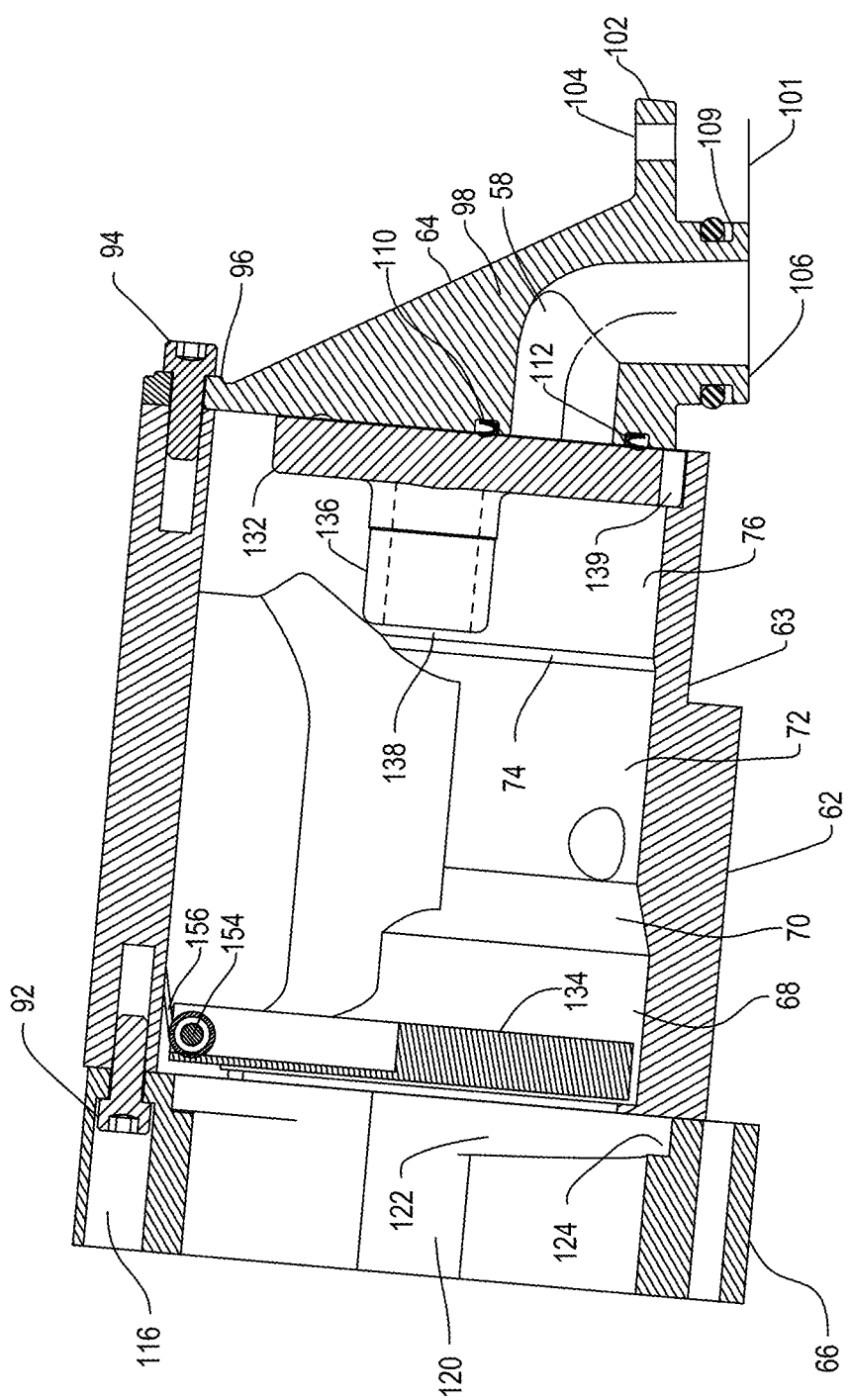
FIG. 5 is a cross sectional view of the manifold receiver when empty.

From FIGS. 4 and 5 it can be seen that receiver housing 62 has a generally cylindrical shape. A rib 61 extends along the top of the manifold receiver housing 62. Also the proximal end of the manifold receiver has an outer surface 63 that is stepped inwardly relative to the more distal outer surface. This spacing facilitates the fitting of the receiver 44 to the associated canister cap 40 or 42.

Figure 6:
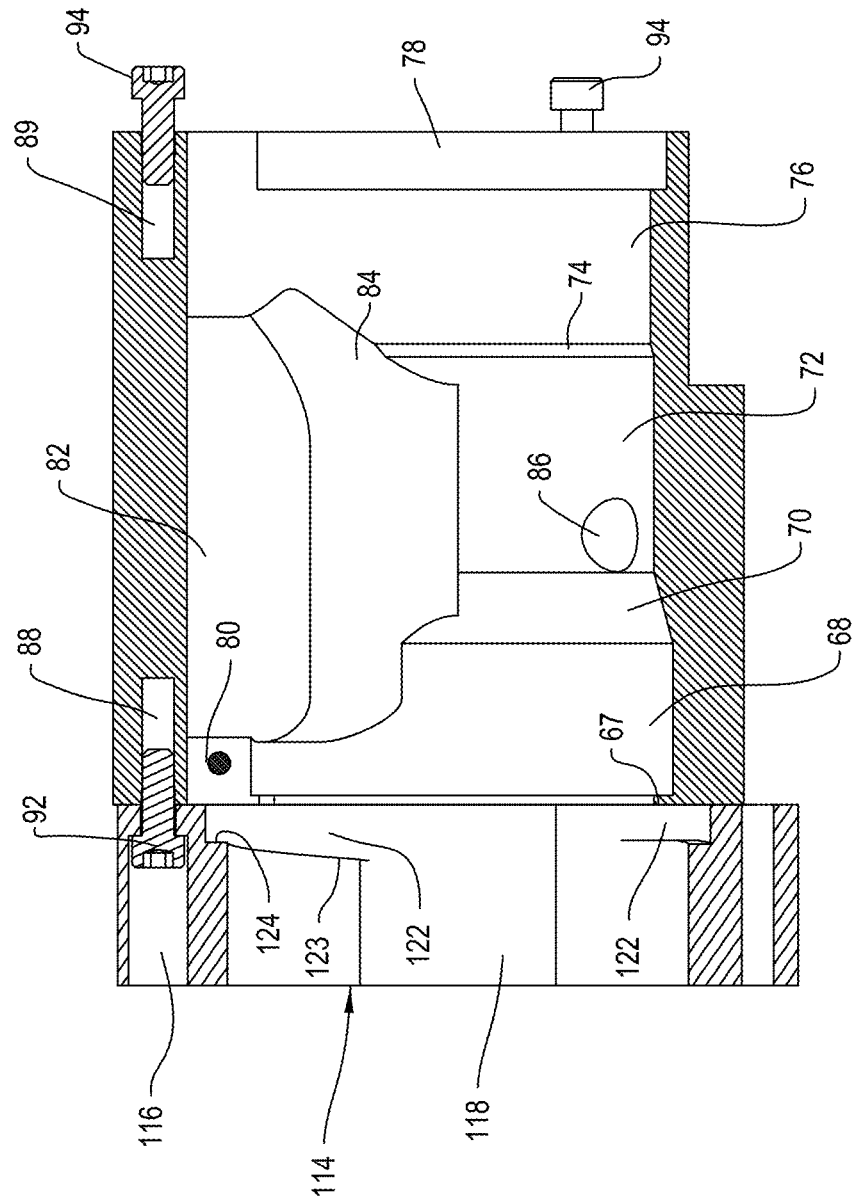
FIG. 6 is a cross sectional view of the manifold receiver housing and lock ring.

Turning to FIG. 6, it can be seen that manifold receiver housing 62 is formed to define a number of bores, void spaces and windows. These voids collectively define a through path through the housing 62 along the longitudinal axis of the housing. At the distal end, housing 62 has cylindrical bore 68. The distal end of receiver housing 62 is formed so as to have a lip 67. Lip 67 extends radially inward into the distal end opening of the housing, this opening being the distal end of bore 68. Immediately adjacent to the proximal end of bore 68 there is a bore 70. The manifold receiver housing 62 is formed so that bore 70 has a diameter that decreases along its length as the distance from bore 68 increases. Bore 70 opens into a second constant diameter bore, bore 72. Bore 72 has a diameter equal to that of the smallest diameter section of bore 70. Proximal to bore 72 manifold receiver housing 62 is formed with a third constant diameter bore, bore 76. Bore 76 has a diameter less than that of bore 72. Between bores 72 and 76 there is a small transition bore 74. Transition bored 74 has a diameter that tapers inwardly from bore 72 to bore 76. At the most proximal end, the manifold receiver housing 62 is formed to have a counter bore 78. Counterbore 78 intersects and has a diameter greater than that of bore 76.

Manifold receiver housing 62 is further formed to have a notch 80. Notch 80 is formed in rib 61 and extends rearwardly from the distal end of the housing and is contiguous with the top of bore 68. Proximal to and contiguous with notch 80, there is a proximally extending void space 82 also defined by an interior surface of rib 61. Void space 82 intersects and extends a slight distance above bores 70, 72, 74 and 76. Void space 82 has a generally rectangular cross section profile. Manifold receiver housing 62 is also formed with two opposed through windows 84 in the sides of housing (one seen in FIG. 6). Each window 84 opens into the middle and proximal sections of bore 68, bore, 70, bore 72, bore 74, bore 76 and void space 82.

A bore 86 extends downwardly from bore 72 through the bottom of the manifold. Bore 86 is dimensioned to receive a fastener (not shown) used to secure the manifold 46 to the associated canister cap 40 or 42. In some versions of the invention, plural bores 86, each for receiving a separate fastener, are formed in the manifold receiver housing 62. It should be appreciated that housing 62 is shaped so that windows 84 allow access to the bores 86 so that the associated fasteners can be inserted and removed.

Closed end bores 88 and 89 extend inwardly from, respectively the distal, front, and proximal, rear, faces of the manifold receiver housing 62. While only a single one of each bore 88 and 89 is illustrated, plural bores 88 and 89 are present. Each bore 88 receives a fastener 92 used to hold the lock ring 66 to the manifold receiver housing 62. Each bore 89 receives a fastener 94 that holds the manifold receiver housing 62 to the receiver adapter 64

Receiver adapter 64, best seen in FIGS. 4 and 5 includes a front end plate 96. Plate 96 is dimensioned to seat against the proximal end of manifold receiver housing 62 including the open ends of bore 76, counterbore 78 and void space 82. Not identified are the through bores in plate 96 in which fasteners 94 extend. While plate 96 covers most of the open distal end of receiver housing counterbore 78, the plate does not cover the whole of the counterbore. Instead, there, at the bottom of the proximal end of the manifold receiver housing 62 a small portion of counterbore 78 remains exposed.

Extending proximally from and integrally formed with plate 96 adapter 64 has a bracket 98. Bracket 98 has a triangular profile such that the overall width across the bracket increases from top to bottom along the length of the plate 96. A tab 102 extends proximally rearwardly from the base of the bracket 98. Tab 102 is formed with an opening 104. Opening 104 receives a fastener (not illustrated) that secures the receiver adapter 64 to the canister cap 40 or 42.

Figure 8:
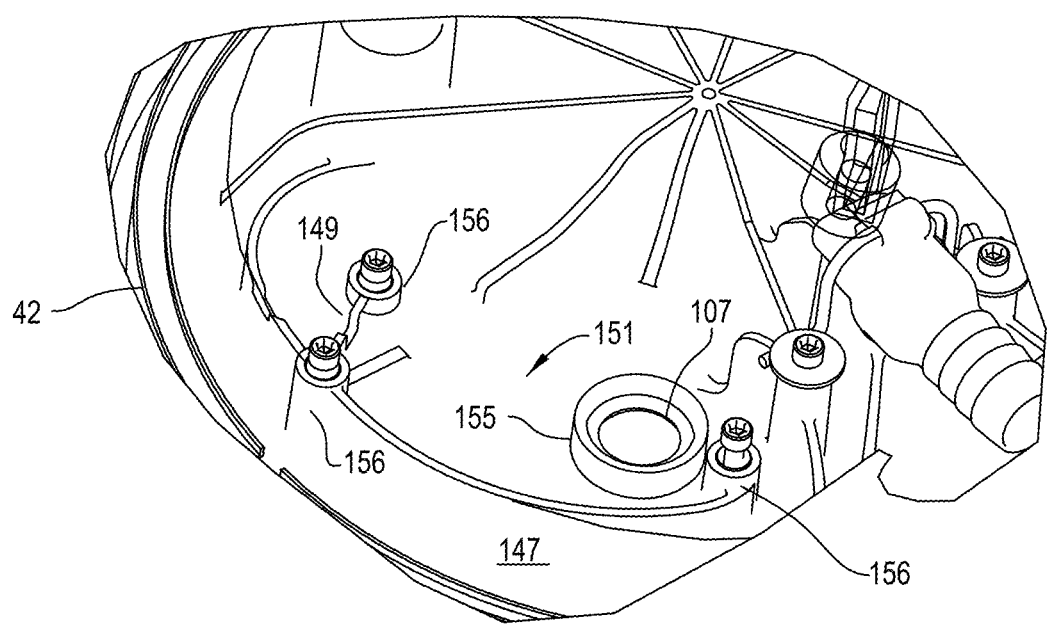
FIG. 8 is a perspective view of a portion of the canister cap to which the manifold receiver is attached.

Conduit 56, the conduit that provides a fluid communication path from the receiver housing 62 to the associated canister 36 or 38, is elbow shaped, so as to have a bend between 80 and 90°. The distal end of conduit 56 opens into the exposed face of plate 96. From plate 96, conduit 56 extends through the lower portion of bracket 98. The proximal end of the conduit 56 extends axially through a boss 106 also part of the receiver adapter 64. Boss 106 extends below bracket 98. When manifold receiver 44 is mounted to the associated canister cap 40 or 42, boss 106 seats in an opening 107 formed in the cap, (FIG. 8). An O-ring 108 is seated in a groove 109 that extends circumferentially around the boss. When mobile unit 30 is assembled, O-ring 108 provides a seal between the canister cap and the inserted boss 106 of the manifold receiver 44.

Receiver adapter 64 is further formed so that plate 96 is in plane offset from the vertical when tab 102 is on a horizontal axis and boss 106 is vertically aligned. This is seen best in FIG. 5 wherein line 101 represents the horizontal axis. Line 101 is shown to intersect the base of boss 106. More particularly, the adapter 64 is formed so that front end plate 96 is angled less than 90° towards the plane along which tab 102 lies. Adapter 64 should further be constructed so that front end plate 96 is angled at least 45° from the horizontal. Thus, the longitudinal axis of manifold receiver is angled from the horizontal so that the proximal end is below the distal end. This angle is, at a minimum 2° and more often 4°. This angle is typically less than 45° from the horizontal.

Figure 5A:
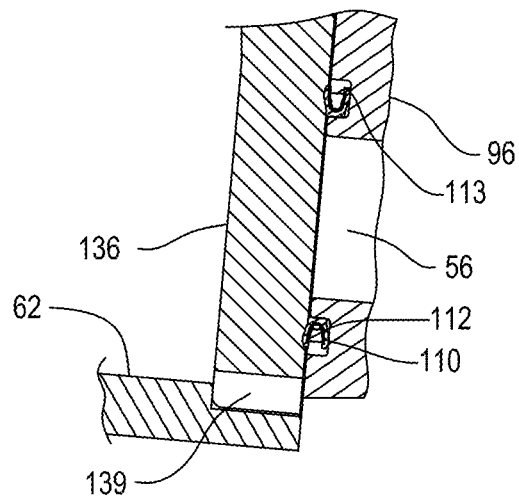
FIG. 5A is an enlarged cross sectional view showing the seal between the receiver adapter front end plate and the valve disk.

Receiver adapter 64 is further formed so that, as best seen in FIG. 5A, an annular slot 110 is formed in the distally directed face of plate 96. Slot 110 is concentric with, surrounds and is spaced away from the opening in plate 96 into conduit 56. A seal 112 is disposed in slot 110 for reasons apparent below.

Lock ring 66, now described by reference to FIGS. 2, 5 and 6, is generally ring shaped. Thus, the lock ring 66 is shaped to have a center located through opening 114. A number of bores 116 extend longitudinally through the ring. Bores 116 receive fasteners 92 used to hold the lock ring 66 to the manifold receiver housing 62.

The lock ring 66 is further formed to define a pair of slots 118 and 120. Slots 118 and 120 are contiguous with through opening 114 and extend radially outwardly from opening 114 to the proximal end of the lock ring 66. While slots 118 and 120 are diametrically opposed, the slots do not have the same arcuate profile. Slot 118 (FIG. 6) subtends an arc that is greater than the arc subtended by slot 120 (FIG. 5). Both of slots 118 and 120 extend the length of the lock ring 66. At the proximal end, lock ring 66 is further formed to have a pair of grooves 122. Each groove is arcuately shaped and is formed in the inner portion of the lock ring that defines opening 114. Each groove 122 is also contiguous with one of slots 118 or 120. Grooves 122 are generally diametrically opposed to each other. Owing to the abutment of the proximal end of the lock ring 66 against the distally directed face of the receiver housing 62, grooves 122 function as slots through which tabs integral with the manifold 46 travel as is described below.

The distal end base of each groove 122 is defined by arcuate stepped interior surfaces 123 and 124 internal to the lock ring 66. Surface 123 extends outwardly from the adjacent surface that defines slot 118 or 120. Surface 123 does not extend perpendicularly from the adjacent slot 118 or 120. Instead, surface 123 is angled, so as to extend proximally towards the adjacent receiver housing 62. Surface 124 extends from surface 123. Surface 124 is parallel to the adjacent proximal end face of lock ring 66.

Manifold receiver 44 has two major moving components. A valve disk 132 normally covers the opening into conduit 56 formed in the distally receiver adapter front end plate 96. A door 134 extends over the distal end opening into the manifold receiver housing 62 when a manifold is not attached.

Valve disk 132, seen best in FIG. 5, is a disk shaped member disposed in the proximal end of the manifold receiver housing 62. More particularly, the valve disk 132 is seated in the cylindrical space defined by counterbore 78. Collectively, the manifold receiver housing counterbore 78 and the valve disk 132 are formed so that the valve disk can rotate in the counterbore.

Valve disk 132 is formed to have cylindrical boss 136 that extends distally forward into manifold receiver housing bore 76. A bore 138 (shown in phantom) extends through both boss 136 and the portion of the valve disk from which the boss extends. The valve disk 132 is formed so that the boss is centered along an axis that is radially offset from the longitudinal axis through the valve disk, the axis around which the valve disk rotates. The valve disk 132 also is formed so as to have a notch 139. Notch 139 extends inwardly from the outer perimeter of the valve disk. Relative the center axis of the valve disk 132, notch 139 is located on the side of the disk opposite the side from which boss 136 extends.

Thus, manifold receiver 44 is constructed so that, when the valve disk 132 is in a specific rotational position within the manifold receiver housing 62, the valve disk covers the receiver adapter front end plate opening into conduit 56. When valve disk 132 is in the above closed state, the disk is further shaped so that notch 139 is located in the base of receiver housing counterbore 78. Valve disk 132 is rotatable to align bore 138 with the conduit opening When the manifold receiver 44 is assembled, seal 112, best seen in FIG. 5A, abuts the proximally directed face of valve disk 132. In one version of the invention, seal 112 is a C- or U-shaped seal. A spring 113 presses the opposed sides of the seal outwardly. Thus, one side of seal 112 presses against the surface of the manifold receiver plate that defines the base of slot 110. The opposed side of seal 112 abuts the proximally directed face of valve disk 132. Seal 112 thus prevents material flow into the interstitial gap between receiver adapter plate 96 and the valve disk 132.

The force generated by spring 113 also drives valve disk 132 against the proximally-directed inner surface of the receiver housing 62 that defines the base of counterbore 78. Thus, spring 113 blocks the free rotation of the valve disk. However, seal 112 and spring 113 are selected so that the anti-rotational force these components collectively place on valve disk 132 can be overcome by application of manual force.

Figure 7:
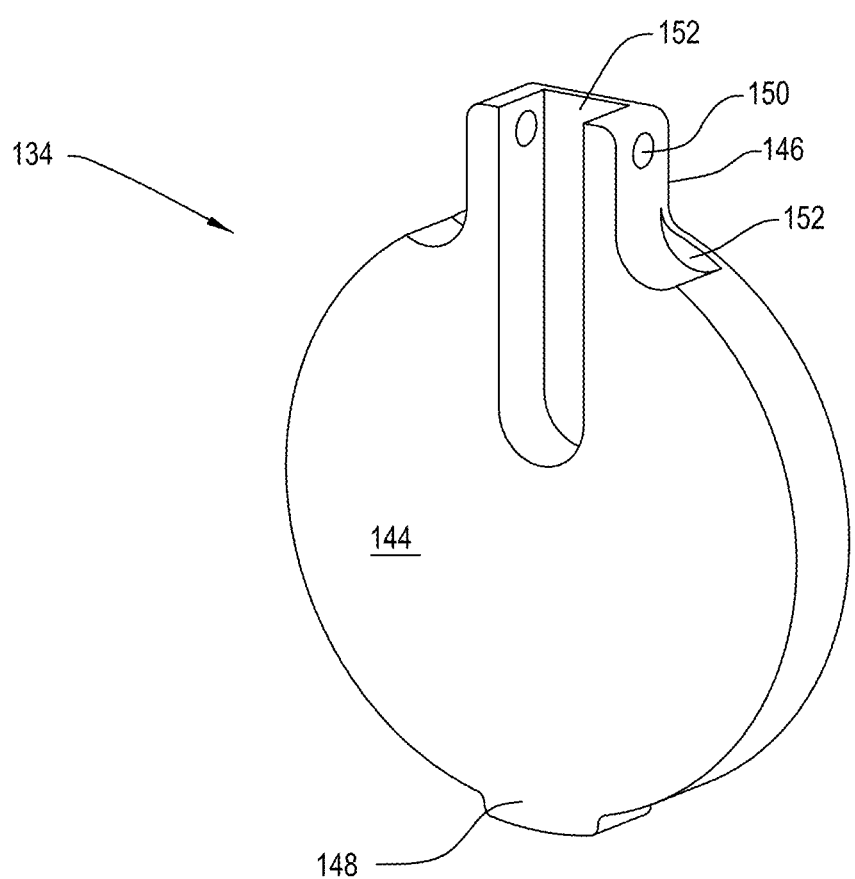
FIG. 7 is a perspective view of the manifold receiver door.

As seen in FIG. 7, door 134 has a cylindrical head 144. Diametrically opposed ears 146 and 148 extend radially outwardly from head 144. A first ear, ear 146, extends a relatively long distance away from the center of the head. Ear 146 is formed to have a through hole 150. Through hole 150 extends through the top of an ear 146 along an axis that is perpendicular to the center axis through the door head. Door 134 is further formed so as to have a slot 152 on the proximally-directed face of the plate. Slot 152 extends from the outer perimeter of ear 146 and along the width of the ear so as to intersect through hole 150. Slot 152 is located along a line that is perpendicular to the axis along which through hole 150 is centered. Slot 152, in addition to extending through ear 146, extends partially into door head 144.

The door is further formed so that adjacent where the sides of ear 146 extend outwardly, there are notches in the head 144. Ear 148 extends a shorter distance away from the center of door head 144 than ear 146. Ear 148 is a solid arcuate structure that extends a relatively short distance away from door head 144.

Door 134 is pivotally mounted to manifold receiver housing 62 as best seen in FIG. 5. Specifically, door ear 146 is seated in notch 80. A pin 154 that extends through the manifold receiver housing 62, and through door hole 150, pivotally holds the door to the manifold housing. A torsion spring 156 is disposed around the section of pin 154 that passes through door slot 152. One leg of the torsion spring bears against the interior surface of the receiver housing rib 61 that defines the top of void space 82. This leg remains static. The second leg of the torsion spring abuts the surface of the door that defines the base of slot 152.

Collectively, manifold receiver housing 62 and door 134 are dimensioned so that, when the manifold 46 is seated in the receiver housing, the door is disposed in void space 82. When the manifold 46 is withdrawn from the manifold receiver 44, there is sufficient clearance between the interior surfaces of the receiver housing that define bores 68, 70 and 72 and plate head 144 and ear 148 that the door pivots downwardly. The sides of the door 134 pivot through windows 84. The manifold receiver housing 62 and the door 134 are further formed so that, when the plate pivots downwardly, the plate ear 148 abuts the inner, proximally directed face of receiver housing lip 67.

FIG. 8 illustrates the portion of canister cap 42 to which the manifold receiver 44 is attached. Cap 42 includes an upwardly extending boss 155. Boss 155 defines the opening 177 in which receiver boss 106 and O-ring 108 are seated. Posts 156 also extend upwardly from cap 42. Posts are the support members over which the receiver housing 62 and receiver adapter 64 are seated. Fasteners 145 hold the receiver housing 62 and receiver adapter 64 to the posts 156.

Cap 42 has a dome-type profile wherein the perimeter of the cap is lower than the center. An arcuate web 147 extends upwardly from perimeter of the cap. Web 147 extends between the two outermost posts. Web 147 thus extends around boss 155. A small web 149 extends upwardly from the post 156 from which web 149 extends that is spaced from boss 155. Collectively, the downwardly inclined surface of cap 42, webs 147 and 149 and the posts 156 at either side of web 147 define a pocket 151 on the top of the cap 42. Pocket 151 partially surrounds boss 155.

III. Manifold

Figure 9:
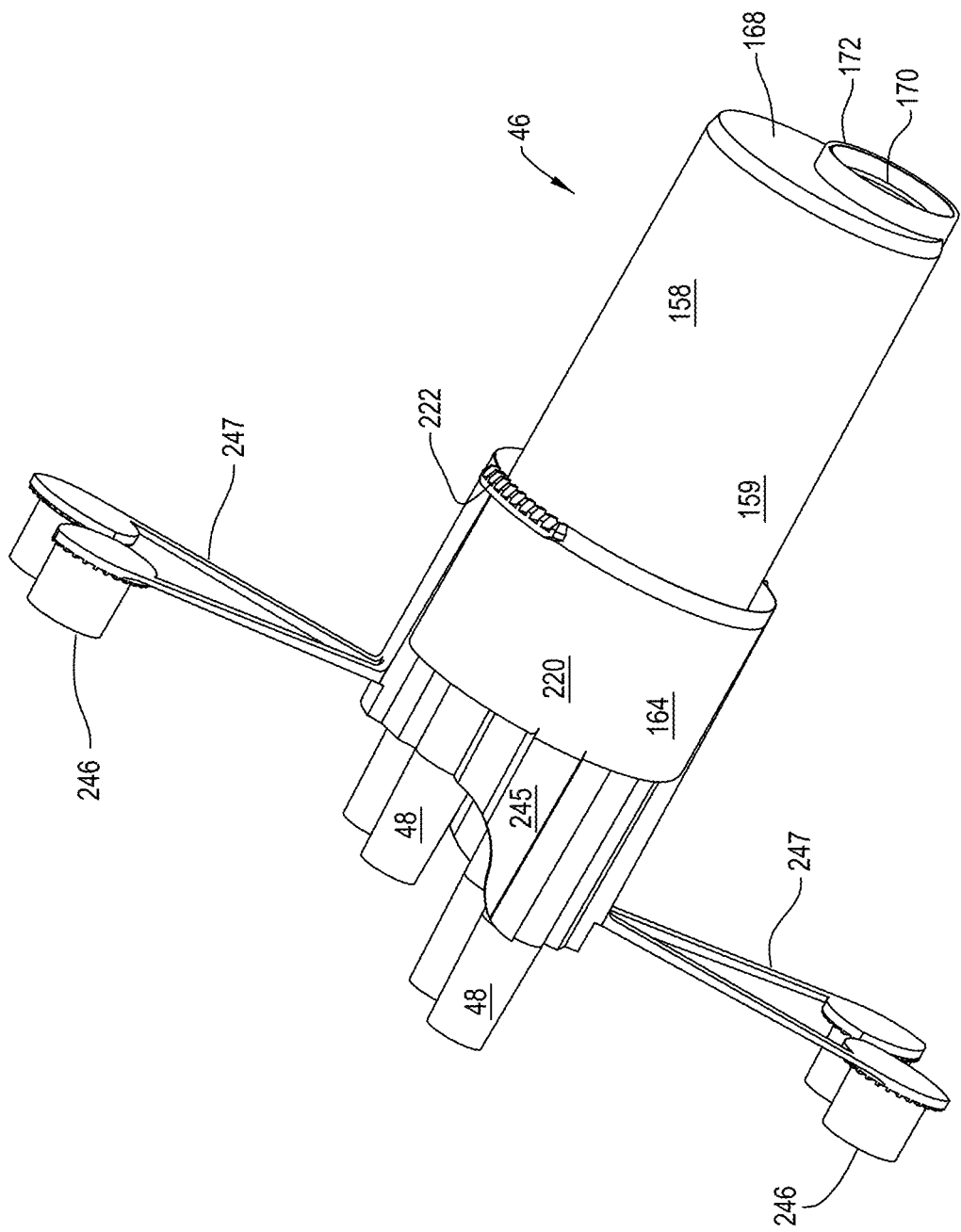
FIG. 9 is a perspective view of the manifold.
Figure 10:
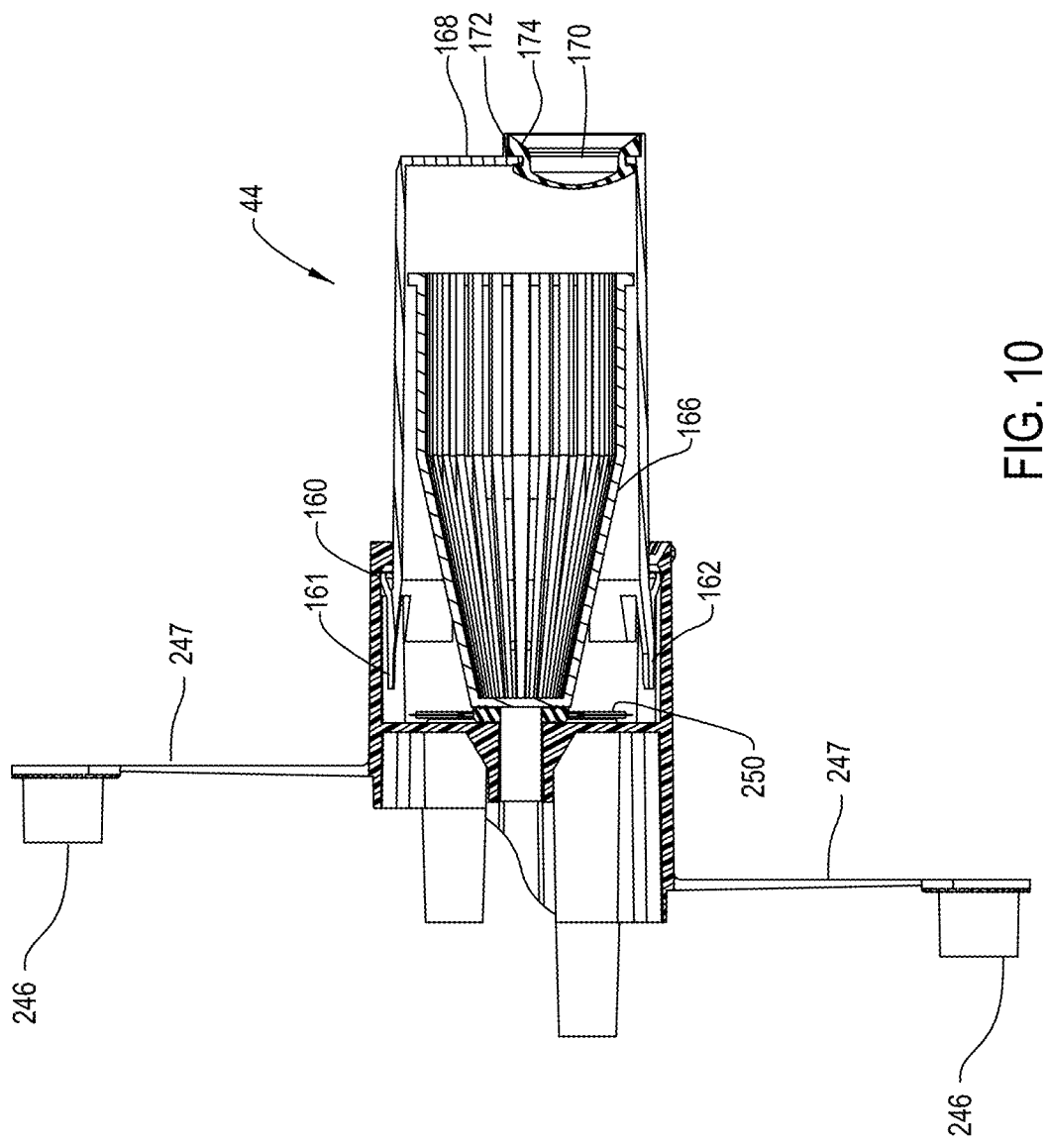
FIG. 10 is a cross sectional view of the manifold.

FIGS. 9 and 10 provide a view of the basic components of manifold 46. There most proximal section of the manifold is an open ended shell 158. A cap 164 covers the open distal end of the shell 158. Collectively, shell 158 and cap 164 form the manifold housing. Internal to this housing is a void space (not identified). Cap 164 is the manifold component from which fittings 48 extend. A filter basket 166 is disposed inside the manifold void space. Filter basket 166 prevents large bits of solid matter from flow downstream.

In more detail, it is understood that manifold shell 158 has a generally cylindrical shape. The shell 158 is formed to have a circular proximal end base 168 from which a tubular shaped side wall 159 upwardly extends. A lip 160 extends circumferentially around the open top end of side wall 159. Lip 160 projects radially outwardly. Two fingers 161 and 162 extend distally upward from the top of side wall 159. Each finger 161 and 162 has an arcuate cross sectional profile. Fingers 161 and 162 are centered on parallel longitudinal axis and are diametrically opposed to each other. Finger 161 subtends a relatively large arc. Finger 162 subtends a relatively short arc.

An opening 170 is formed in the shell base 168. The opening is dimensioned to receive valve disk boss 136. The shell is formed so that opening 170 is centered along an axis that is off center to the longitudinal axis of the shell 158. A circular lip 172 extends downwardly from the shell base 168 around opening 170. Lip 172 is spaced radially away from the annular section of the shell base 168 that defines the outer perimeter of opening 170. In one versions of the invention, manifold shell 158 is formed so that a small arcuate section of the lip is essentially flush with an adjacent section of the shell side wall 159.

Figure 12:
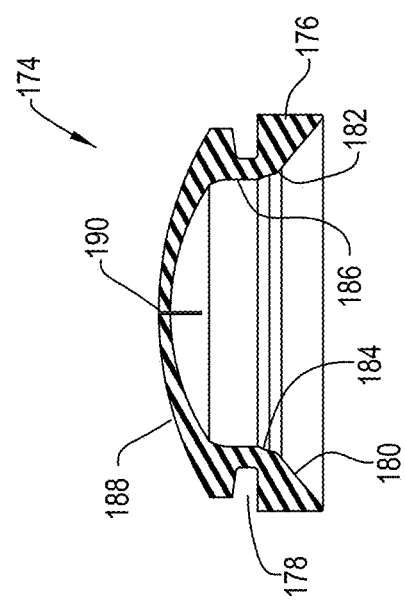
FIG. 12 is a cross sectional view of the manifold drip stop.
Figure 11:
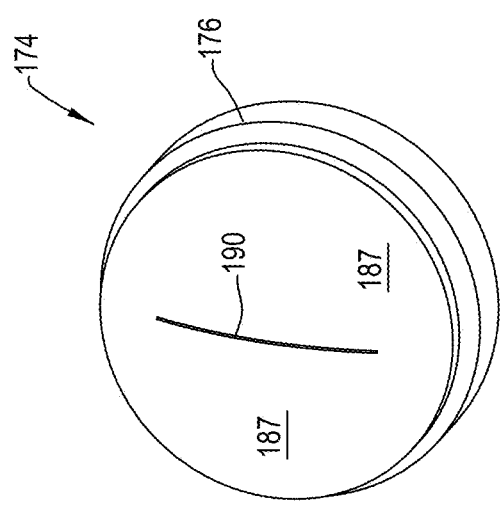
FIG. 11 is a perspective view of the manifold drip stop.

A drip stop 174, now described by reference to FIGS. 11 and 12 is fitted in manifold opening 170. Drip stop 174 is formed from a compressible material such as polyisoprene rubber. The drip stop 174 has a ring shaped base 176. Base 176 is formed so as to have around its outer perimeter a slot 178. When manifold 46 is assembled, the drip stop 174 seats in opening 170 so the perimeter section of base 168 that defines the opening seats in slot 178. The section of the stop base 176 below the slot defining section seats inside the enclosed space defined by shell lip 172.

Drip stop base 176 is further shaped so that, extending forward from the proximal end, the drip stop has first, second and third inwardly tapered annular surfaces 180, 182 and 184, respectively. Relative to the longitudinal axis extending through the drip stop 174, surface 180 has a taper greater than that of surface 182, surface 182 has a taper greater than that of surface 184. In terms of overall length, surface 180 extends a longer distance along the length of the valve base than lengths of surfaces 182 and 184 combined. Immediately above the top most tapered surface, surface 184, valve base 176 is shaped to have a constant diameter inner surface 186. Surface extends across and above the portion of the valve base 176 in which slot 178 is formed.

The diameter of inner surface 186 is greater than the outer diameter of valve boss 136 by approximately 0.5 and 1.0 mm. Collectively the relatively wide diameters of drip stop inner surfaces 180-186 relative to the valve boss allow the base of the drip stop to function as a lead in for the valve boss 136. This lead in corrects for minor misalignment of the valve disk 132.

Drip stop 174 has a head 188 with a concavo-convex profile that is integral with and projects distally forward from base 176. Drip stop head 188 consists of two lips 187. Normally, lips 187 abut so as to define a slot 190 therebetween. Slot 190 extends along a two diametrically opposed radial lines. The slot 190 does not extend across the whole of the width of the valve head 188. In order for the drip stop to perform a sealing function when seated over the valve boss, slot 190 has a length less than the outer diameter of the valve boss. The normal abutment of the opposed lips 187 of drip stop head 188 blocks flow out of manifold opening 170.

Figure 13:
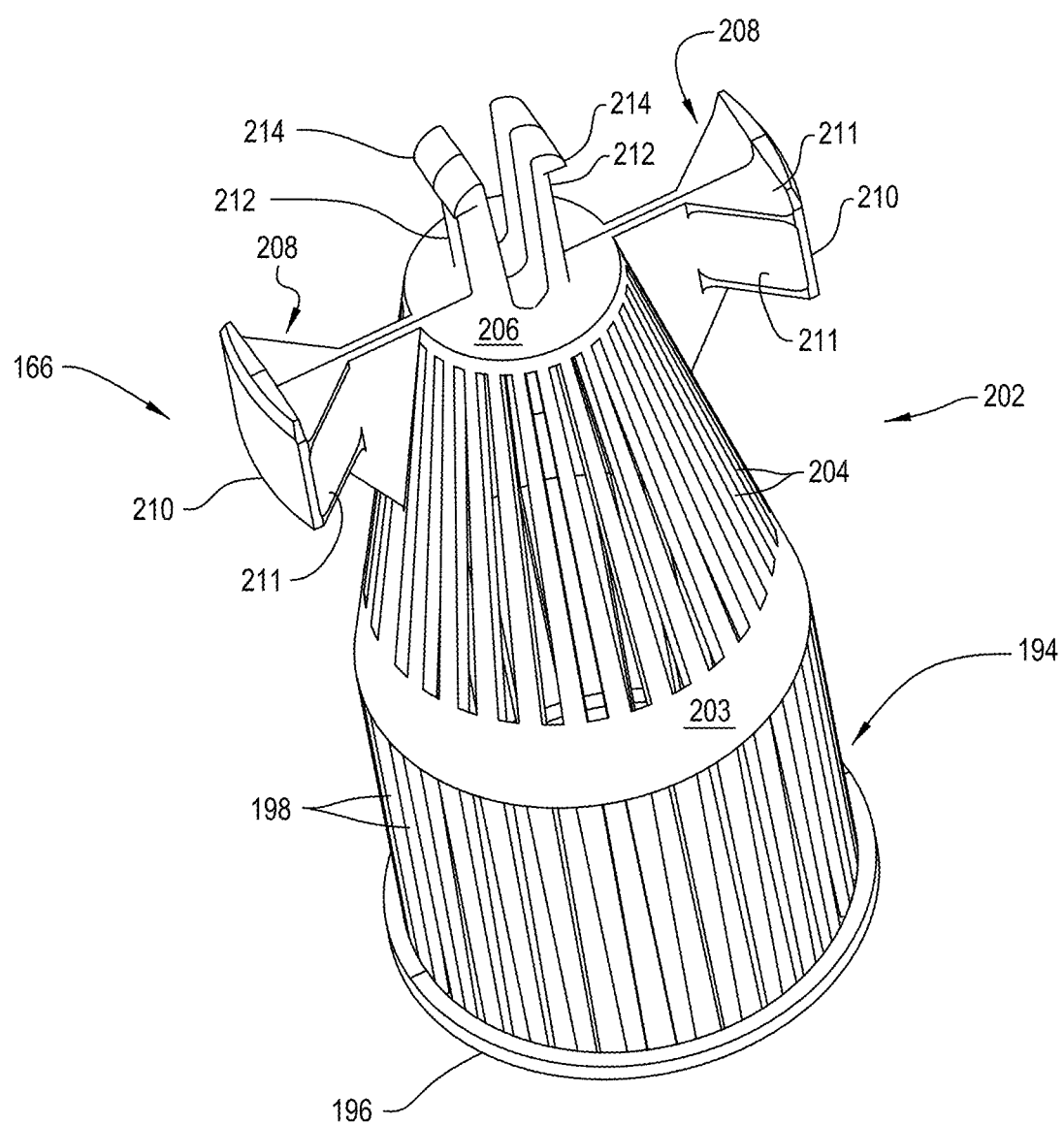
FIG. 13 is a perspective view of the filter basket internal to the manifold.

The filter basket 166, now explained by reference to FIGS. 10 and 13. The filter basket 166 is shaped to have a cylindrical trunk 194. Specifically, the trunk 194, at its proximal end base, has a ring 196. Extending upwardly from the inner surface of the ring 196 are a number or arcuately spaced apart ribs 198. Ribs 198 are spaced apart from each other so as to be separated by a maximum distance of 10 mm or less and, more preferably, 5 mm or less. Thus, large sized bits of solid matter in the waste stream are blocked from downstream flow by the filter basket 166. Filter basket 166, it is further understood is shaped so that ribs 198 are spaced at least 1 mm apart. This prevents small bits of solid and semi-solid waste from being trapped by the basket 166 and clogging the manifold 46.

Above trunk 194, filter basket 166 has an inwardly tapered neck 202. Neck 202 generally has the shape of a slice section through a cone. At the base of the neck there is a circular, inwardly tapered web 203. Web 203 is the structural component to which the distal ends of the ribs 198 extend. A set of arcuately spaced apart ribs 204 extend upwardly and inwardly from web 203. Ribs 204 terminate at a disk shaped member that forms the filter basket head 206.

A pair of diametrically opposed arms 208 extend outwardly from opposed sides of the filter basket neck 202. Each arm 208 is a generally planar structure. The arms are in a common plane that intersects the longitudinal axis of the filter basket 166. The top surfaces of the arms 208 are coplanar with filter basket head 206. A hand 210 is located at the free end of each arm. Each hand 210 is generally oriented so as to be perpendicular to the associated arm 208. Each hand 210 has an outer surface (not identified) that has an arcuate profile. Reinforcing webs 211 at the top bottom of each hand 210 further connect each hand to the associated arm 208.

Two elongated, parallel ears 212 extend distally forward from the top of the filter basket head 206. Each ear 212 is generally in the form of a post with a rectangularly shaped cross sectional profile. Each ear 212 is further shaped to have a tip 214 that projects a short distance outwardly towards an adjacent arm 208. For reasons that are apparent below, it should be understood that the ears have a slight degree of flexibility relative to the rest of the filter basket 166.

The manifold cap 164, now described by reference to FIGS. 14, 15 and 16, is formed from a single piece of polypropylene or similar plastic. The manifold cap 164 is shaped to have a cylindrical tube-shaped skirt 220. At the proximal end base of the skirt 220, two tabs 222 and 224 project radially outwardly. Tabs 222 and 224 are diametrically opposed from each other. The tabs 222 and 224 do, however, subtend different arcs. Tab 222 subtends a relatively large arc; this tab is designed to slip fit into manifold receiver lock ring slot 118. Tab 224 subtends a shorter arc; this tab is designed to slip fit into manifold receiver lock ring slot 120.

Cap skirt 220 is further formed to have a rim 217 that defines the proximal end opening of the skirt that is inwardly tapered. Above rim 217, the skirt 220 has an outwardly directed step 218 that extends circumferential around the interior of the skirt. Cap 164 is dimensioned so that the inner diameter of skirt 220 above step 218 is less than the outer diameter of shell lip 160 by approximately 0.5 mm. Thus, when the manifold 46 is assembled, the shell is inserted into cap 164 so that the lip seats on skirt step 218. The compression of the inner surface of the cap skirt 220 around the cap lip 160 substantially eliminates loss of suction between the cap and the skirt.

A number of ribs extend inwardly from the inner surface of the manifold cap skirt 220. These ribs, it is understood start at positions located above step 218. There is a pair of adjacent ribs 226 and a pair of adjacent ribs 228. The line around which ribs 226 are centered is diametrically opposed to the centerline around which ribs 228 are centered. Relative to ribs 226, ribs 228 are arcuately spaced apart from each other a relatively short distance. More particularly, ribs 226 are spaced apart a sufficient distance from each other so that shell finger 161 can be slip fitted therebetween. Ribs 228 are spaced apart a sufficient distance so that finger 162, not finger 161, can be slip fitted therebetween. Shell fingers 161 and 162 and cap rib pairs 226 and 228 thus facilitate the proper alignment of the manifold shell 158 and cap 164 when these components are assembled together.

Manifold cap skirt 220 also has two pairs of ribs 230 (one pair seen in FIG. 14). Each pair of ribs 230 are arcuately spaced apart a sufficient distance from each other so that one of the filter basket hands 210 can be slip fitted therebetween.

A disk shaped head 234 extends over the top end of manifold cap skirt 220. Head 234 is formed so as to have a center-located through hole 236. Through hole 236 is rectangularly shaped. Cap 164 is further formed so as to have a rectangular post 238 that extends upwardly from the head 234. Post 238 is centered around through hole 236 and is hollow so as to allow access to the through hole.

Fittings 48 extend upwardly from head 234. Each fitting 48 is in the form of a hollow tube. Ports 237 in the cap head 234 provide fluid communication openings between each fitting and the interior void space of the manifold 46. A circular rib 239 projects downwardly from the inner face of the cap head and extends around each port 237. As seen in FIG. 16, each rib 239 is shaped to have an outer surface 240 that curves outwardly away from the adjacent proximally directed face of cap head 234. Outer surface 240 transitions to a constant height inner surface 241. Rib inner surface defines the perimeter of the associated port 237.

A fence 245, seen best in FIGS. 2 and 9, extends upwardly from cap head 234. The fence 245 is in four separate sections (sections not identified). Each fence section extends between two adjacent fittings 48. The fence 245 is located a short distance inwardly from the outer perimeter of cap head 234. Fence 245 functions as the manifold member an individual can hold on to in order to insert, rotate and remove the manifold in the below procedures.

In the illustrated version of the invention, two adjacent fittings 48 are of short length. The remaining two fittings 48, which are adjacent each other, are longer. Fittings 48 are so sized to reduce the effort required to fit a suction line 50 to each fitting.

A removable cap 246 is provided for each fitting 48. Each fitting cap 246 is integrally attached to the manifold cap by a tether 247. The fitting caps 246 and tethers 247 are part of the same plastic piece part from which the rest of the manifold cap 164 is formed.

Figure 18:
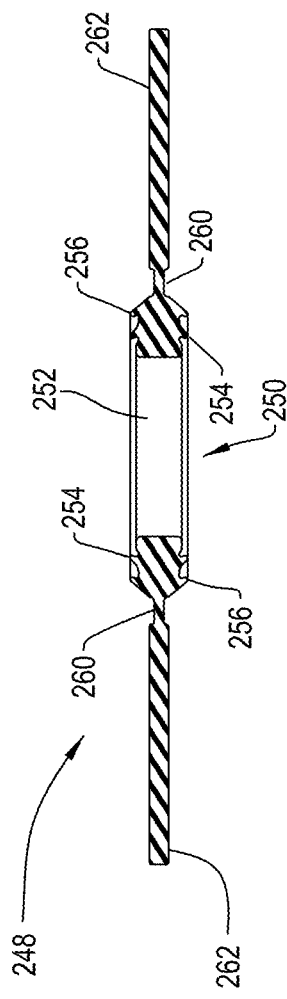
FIG. 18 is a cross sectional view of the flapper valve.
Figure 17:
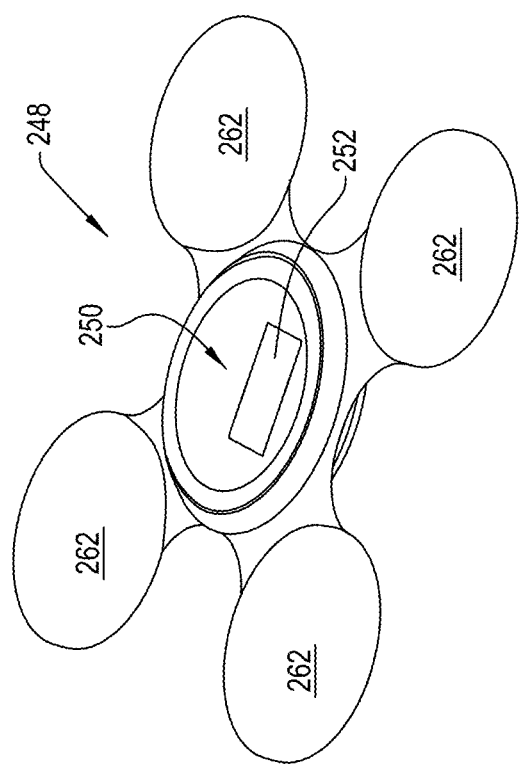
FIG. 17 is a perspective view of the flapper valve internal to the manifold.

Manifold 46 of this invention also has a flapper valve unit 248, now described by reference to FIGS. 10, 17 and 18. Flapper valve unit 248 is formed from a single piece of compressible, flexible material such as polyisoprene or other elastomeric material. Flapper valve unit 248 has a disk shaped hub 250. Hub 250 is formed with a center through hole 252. Hole 252 is dimensioned to receive filter basket ears 212. The flapper unit hub 250 also has a number of annular ribs 254 and 256. One rib 254 extends outwardly from the opposed distally and proximally directed faces of hub 250. One rib 256 also extends outwardly from each of the opposed faces of hub 250. Ribs 254 are located proximal to hub through hole 252. Ribs 256 surround ribs 254. Each rib 254 and 256 has an inwardly angled cross sectional profile. Thus, each rib 254 and 256 extends outwardly from the hub face and is angled so as to be directed to the longitudinal axis through hub hole 252.

Flapper valves 262 are pivotally connected to and extend from hub 250. Each flapper valve 262 covers a separate one of the fitting ports 237. A hinge 260, also an integral part of the flapper valve unit 248, pivotally connects each flapper valve 262 to the hub 250. Hinges 260 are formed out of sections of the material from which the valve is formed have a thinner cross sectional thickness than the adjacent hub 250 and flapper valve 262.

Each flapper valve 262 is generally disk shaped. Each flapper valve 262 is dimensioned to cover both the associated port 237 and to abut over the rib 239 that surrounds the port. Generally each flapper valve 262 has a diameter that is approximately 4 mm greater than the inner diameter of the associated port-defining rib 239

As discussed below, when manifold 46 is assembled, flapper valve unit hub 250 is compressed between the manifold cap 164 and filter basket 166. This compression causes slight outward expansion of the hub 250. Thus, when designing the flapper valve unit 248, care must be taken to ensure that, when the hub is in the expanded state, the flapper valves 262 still seat over the complementary cap ribs 239. Further, when in this expanded state the flapper valves 262 should not be in contact with the inner surface of the cap skirt 220. Such contact could inhibit the ability of the valves to rapidly open and close.

Also, design of the components forming manifold 46 should be such that, when assembled, the flapper valves 262 are slightly spaced above or only lightly contact the adjoining ribs 239. If, upon manifold assembly, flapper valves 262 press relatively tightly against the ribs 239, the valves may be in a static state wherein they are already pivoted slightly open. If a flapper valve 262 is in this state, the valves ability to block reverse flow out of the manifold 46, through the associated fitting 48, is reduced.

Manifold 46 is assembled by first fitting the valve unit 248 over filter basket ears 212. Owing to the complementary rectangular profiles of the ears 212 and the hub through hole 252 in which they are seated, filter valve unit 248 is blocked from rotating. Filter basket 166 is then snap fitted to cap 164. This is accomplished by pressing the filter basket ears 212 through cap hole 236 and the hollow of post 238. Upon emerging from post 238, ear tips 214 project beyond the top edges of the walls defining the post so as to lock the filter basket 166 to the cap 164.

As a consequence of the securement of filter basket 166 to cap 164, flapper valve unit hub 250 is compressed between these components. Ribs 254 and 256 function as seals that prevent loss of vacuum through manifold cap hole 236. Since two ribs, seals, are present on each side of the flapper valve unit 248, only minimal compressive pressure needs to be present between the ribs 254 and 256 and the adjacent static surfaces in order to affect the desired fluid-tight barrier. This force is less than force required to compress the solid body of the seal hub 250. Thus it should be appreciated filter basket ears 212 and cap post 238 are collectively dimensioned so that, upon assembly of the manifold, ribs 254 and 256 are compressed, but not over compressed, between the cap and filter basket.

Moreover, as discussed above, ribs 254 and 256 are inwardly directed. Consequently, when a vacuum is drawn, the ambient atmosphere is present through cap through hole 236 around the base of filter basket ears 212. This air forms a pressure head around the inner surfaces of ribs 254 and 256. This pressure head urges the inwardly directed ribs 254 and 256 outwardly. The ribs 254 and 256 are thus flexed against the adjacent static surface; either the distally directed face of filter basket head 206 or the proximally directed face of cap head 234. This abutment of the ribs 254 and 256 against these adjacent surfaces increases the integrity of the fluid barrier formed by these ribs.

Further, the square ears 212-in-square hole 252 prevents the filter unit from rotating during the assembly process. This ensures that, upon assembly, each flapper valve 262 is disposed under a separate port defining rib 239.

Also, manifold 46 is constructed so that the outer diameter of filter basket lip 196 is less than the inner diameter of manifold shell side wall 159. The difference in these two dimensions is equal to or less than the width of the gap defined by filter basket ribs 198. Consequently, upon assembly of manifold 46, there is a small gap between the inner surface of side wall 159 and filter basket lip 196. This gap functions as a flow through path through which liquid and small bits of matter that will not clog the downline components can pass through the manifold.

IV. Operation

Prior to use, before the manifold 46 is fitted to the mobile unit 30, manifold receiver 44 is in the state as depicted in FIG. 5. Specifically, valve disk 132 is in the index position so that the body of the valve disk is closed over the opening in plate 96 to receiver adapter conduit 56. Spring 156 holds door 134 closed. Collectively, door 134 and spring 156 inhibit curious fingers from entering the manifold receiver housing 62.

Mobile unit 30 is prepared for use by fitting the manifold 46 to the complementary receiver 44 associated with the canister 36 or 38 in which the waste drawn from the surgical site is to be collected. This step is performed by inserting the manifold 46 into the receiver so that manifold shell base 168 is directed to the valve disk 132. For mobile unit 30 to function, valve disk boss 136 must seat in shell opening 170. Lock ring slots 118 and 120 and manifold tabs 222 and 224 cooperate to ensure this alignment of the manifold 46 to the valve disk 132. Specifically, these components are positioned so positioning of manifold tab 224 in receiver slot 118 results in the manifold 46 being rotationally positioned so that shell opening 170 is aligned with valve disk boss 136. After the manifold is so positioned, continued insertion of manifold 46 into the receiver housing 62 results in shell base fitting over the valve disk boss 136.

Once the manifold 46 is fitted against valve disk 132, the manifold is rotated. The direction of rotation is dictated by the fact that manifold tabs 222 and 224 can only rotate into lock ring slots 120. As a consequence of the rotation of the manifold, the valve disk boss 136 and, by extension, the whole of the valve disk 132, undergoes a like rotation. This rotation places valve bore 138 in registration with the receiver adapter distal end opening into conduit 56. Also, as result of the rotation of the manifold 46 and the valve disk 132, the manifold is positioned so that manifold opening 170 is, in a rotational position, at the bottom of the manifold.

Thus, manifold opening 170 functions as a keyhole for receiving valve disk boss 136. Valve disk boss 136 functions as a drive member that rotates the valve disk 132 to the open state.

The rotation of the manifold 46 results in more than a like rotation of valve disk 132. From the above discussion, it should be clear that when the manifold is seated in the receiver housing, valve lips 187 initially extend over valve boss 136. This initial abutment of the manifold drip stop 174 against the valve disk boss 136 blocks further movement of the boss through the drip stop. However, as the manifold 46 is rotated, surfaces 123 internal to the lock ring 66 function as cam surfaces against which manifold tabs 222 and 224 abut. These surfaces 123 are directed proximally rearward. Therefore, as the manifold turns, the abutment of the tabs 222 and 224 against the proximally directed surfaces 123 results in the manifold being driven in the like proximal direction. This action results in sufficient force being generated to overcome the elastomeric forces holding drip stop lips 187 in the closed position. Manifold 46 is thus pushed down over the valve boss 136.

At the end of this process, drip stop base 176 is thus disposed over the base of valve boss 136. Valve lips 187 press against the outer circumference of valve disk boss 136. Collectively the drip stop base 176 and lips 187 form a fluid tight barrier between the boss 136 and the surrounding section of manifold shell base 168 that defines opening 170. The distal end of the boss 136 extends through valve head slot 190. The distal end of boss 136, the end that defines the opening into bore 138, is disposed in the bottom of the manifold shell 158.

The process of preparing the mobile unit 30 for use is completed by the coupling of a suction applicator 52 to the unit by a suction line 50. The manifold fitting 48 to which the suction line 50 is to be attached is uncapped and the suction line connected thereto.

Mobile unit 30 is actuated by activating the suction pump 58. Activation of suction pump 58 results in a waste stream being drawn from the surgical site being drawn into the applicator 52, through the suction line 50 and into the manifold 46. This waste stream includes liquid and solid waste to which the suction applicator 52 is applied as well as air adjacent the applicator 52. In the manifold, solid waste entrained in the waste stream having a width greater than the gaps between filter basket ribs 198 is trapped by the filter basket 166 or between shell wall 159 and basket lip 196. The suction force draws the components of the waste stream that flows past the filter basket 166 into the open proximal end of bore 138 integral with valve disk 132. Boss 136 serves as the fitting through which the waste stream flows from the manifold 46 into conduit 56. The barrier formed by the drip stop between the manifold 46 and valve boss 136 prevents loss of vacuum between these components.

From valve disk bore 138 the waste stream flows through the receiver adapter conduit 56 into the associated canister 36 or 38. Liquid and solid components of the waste stream that enter the canister 36 or 38 precipitate out of the stream and are held in the canister 36 and 38 for final disposal.

The fluid stream that travels from the canister 36 or 38 is thus essentially liquid and solid free. Prior to final exhaust of this stream from the suction pump 58, this fluid stream is filtered to remove odor causing components and/or bacterial and viral sized particulates that may be entrained in this fluid stream.

Once the medical/surgical procedure is completed, and use of the mobile unit 30 is no longer required, manifold 46 is removed. The seating of manifold tabs 222 and 224 in the lock ring slots 120 prevent the manifold 46 from just being pulled out of the receiver 44. Instead, it is necessary to first rotate the manifold 46 so that tabs 222 and 224 align in slots 118 and 120, respectively. As a consequence of having to so rotate the manifold 46, the valve disk 132 undergoes a like rotation. The rotation of the valve disk 132 reorients the disk so the disk again covers the open end of the receiver adapter conduit 56.

Once manifold 46 is properly positioned, the manifold is manually withdrawn from the receiver 44. Once valve head 188 passes over the distal end of the valve disk boss 136, the opposed sections of the head that define slot 190 come together so as reclose opening 170. The closing of the opening 170 substantially eliminates leakage of waste material remaining in the manifold.

Post use, the mobile unit 30 is coupled to a docker (not illustrated and not part of this invention.) Waste material in the canister 36 or 38 is flowed through the docker to a treatment facility. The manifold is disposed of as medical waste.

As described above, valve disk 132 normally closes the opening into conduit 56 that leads to the associated canister. To use the system 30, draw a suction through the manifold and upstream components, the manifold must first be properly aligned in order force the appropriate displacement of the valve disk. Then, as a consequence of the removal of the manifold 46, valve disk 132 is returned to its closed stated. Thus one benefit of the system of this invention is that the flow path into the canister is normally closed. Only when a manifold attached is the opening open. Then, as result of the process of rotating the manifold 46 to remove it from the receiver, the valve disk 132 closes this opening. This arrangement blocks the release of gases displeasing to the nose through the manifold receiver 44.

The closure of valve disk 132 does more than prevent the release of noxious gases. Mobile unit 30 has plural canisters 36 and 38. When suction pump 58 is actuated, the suction may be drawn on both canisters. The automatic closure of valve disk 132 when a manifold is not present prevents suction loss through the empty manifold receiver 44.

The manifold receiver 44 and manifold 46 of this invention are further designed so that when the manifold seats over the valve boss 136, the opposed lip 187 of the valve head 188 press against the outer surface of the boss. Owing to the camming action of the manifold tabs 222 and 224 against the receiver 44, this displacement is a result of the application of the rotational "twisting" of the manifold in position. The physical effort one needs to exert when so rotating the manifold for both insertion and removal does not impose an appreciable strain on the arm or hand of the inserter. Also, valve base 176 presses against the valve boss. There is essentially no air flow around these seal-forming components. The absence of this air flow means these components do not engage in a vibrational movement that results in the generation of noise.

Further, in preferred versions of the invention, the cross sectional area of the valve disk bore 138 is at least equal to the cumulative cross sectional areas of manifold cap ports 237. Thus, as the waste stream flows through the manifold 46, the gaseous components of this stream do not engage in noise-generating compression. Further since the gas flow is not compressed, the flow of the fluid into bore 138 does not result in drop in flow rate.

Mobile unit 30 and manifold 46 of this invention are further collectively designed to substantially eliminate leakage of collected waste. Drip stop 174 does more than prevent leakage of waste in the manifold after removal. As the manifold 46 is removed the receiver 44, drip stop lips 187 press against the distal end of the valve boss inside the manifold. Thus, upon removal of the manifold, valve lips 187 wipe adhered waste of the valve boss 136.

The geometry and orientation of the manifold receiver 44 also reduce the leakage of waste from both the mobile unit 30 and the manifold 46. As mentioned above, the receiver adapter 64 is designed so that plate 96 is angularly offset from the vertical. Consequently, receiver housing 62 is angled from the horizontal. By extension, when the manifold 46 is seated in the receiver housing 62, the manifold is similarly offset from the horizontal. More specifically, the shell base 168 is below the manifold cap 164. This means that when the manifold 46 is in the run position, shell opening 170 is located at the lowest elevation of the manifold. This feature ensures that substantially all waste material drawn into the manifold flows out through the valve disk bore 138 and adapter conduit 56 into the canister 36 or 38.

Then, when the manifold 46 is rotated for removal from receiver 44, the side of the base defining opening is rotated upwardly. Waste material still in the manifold flows towards the opposite side of the void space internal to the manifold 46. Thus, upon removal of the manifold from the receiver 44, waste still in the manifold is away from opening 170. This reduced the instances of this waste leaking from the opening.

Also, when the removal of the manifold 46 results in valve disk 132 being rotated back to the closed state, notch 139 is located in the bottom rotational position. Owing to the inclined orientation of the manifold receiver housing 62, liquid in left in the housing will flow towards the valve disk 132. When this liquid reaches the valve disk, it flows out of the receiver 44 through notch 139. This liquid is contained in the pocket 151 formed on the top of the canister cap 40 or 42. Thus, manifold receiver 44 and manifold 46 of this invention are further designed to minimize the accumulation of uncontained waste on the mobile unit 30.

The above angled orientation of the manifold receiver 44 also ensures that, when the mobile unit 30 is in operation, the proximal end base manifold outlet opening 170 is, in a gravity orientation, below inlet ports 237. This makes it unlikely that waste in the manifold can flow upstream, through ports 237, and out the manifold 46.

Flapper valve unit 248 also stops the leakage of waste from the manifold 46. The individual flapper valves 262 normally cover the cap ports 237. When suction pump 58 is actuated, and a fitting cap 246 is removed, the suction drawn by the pump is sufficient to generate a pressure head that flexes the flapper valve 262 of the associated fitting 48 open. The waste stream is thus able to flow into the manifold. When the pump is deactivated, hinge 260 has sufficient resilient force to return the flapper valve against the adjacent rib 239 integral with the manifold cap 164. Upon removal of the manifold from the receiver 44, the flow of waste through the ports 2239 is thus blocked by the flapper valves 262. Further, should manifold 46 be inverted, waste in the manifold moves against these faces of the flapper valve. The mass of this waste thus becomes an added force that holds the flapper valves closed.

Moreover, should a manifold with waste be inverted, the waste presses the flapper valves against the crowns of the adjacent ribs. Owing to the small area of this interface, the force per unit area is relatively high. This focused force therefore enhances the sealing effect of the flapper valves.

Also, as discussed above, the flapper valve unit hub 250 also forms a seal around the filter basket ears 212. This simplifies the manufacture of the manifold 46. Still another feature that simplifies the manufacture of manifold 46 is that both the shell 158 and cap 164 are formed from plastic. These components are further dimensioned so that, when mated together the cap skirt 220 presses against shell lip 160. The compression of these two components against each other forms a substantially fluid tight barrier between these components. Thus, the need to provide an O-ring or other sealing element between the shell 158 and the cap 164 is eliminated.

Mobile unit 30 and manifold 46 are further designed so that if, upon manifold insertion the manifold is slightly out of alignment with the valve boss 136, the valve boss strikes the proximally extending manifold lip 172. Further insertion of the manifold is blocked. Since the boss strikes the lip 172, the likelihood that the boss could inadvertently push the drip stop 174 out of opening 177 is substantially eliminated.

It should likewise be recognized that in preferred versions of the invention, the plastic from which the manifold shell 158 and cap 164 are formed is at least partially transparent. This provides medical personnel with a quick means to verify that the manifold being fitted to the mobile unit 30 is not a used manifold that contains previously collected waste.

Further it should be understood that the axes around which the flapper valves 262 pivot are spaced from the associated cap ports 237. Thus, the minimal pivoting of a flapper valve 262 due to the action of a pressure head acting against the valve results in the immediate establishment of a wide area opening between the manifold cap 164 and the flapper valve 262. Consequently, once the flapper valve is so opened, large amounts can flow essentially unimpeded into the center of the manifold 46.

The narrow gaps between filter basket ribs 198 and 204 block large solids from flowing downstream into the associated canister 36 or 38. Thus, flow of these solid further into the mobile unit 30 where the can possibly adversely affect downline components of the mobile unit or docker not relevant to this invention is prevented. Further, the gaps between ribs 198 and 204 have lengths at least three times (×3) and more often at least five times (×5) their widths. The surface area of the gap-defining filter structure, trunk 194 and neck 202 is, greater than the lateral cross sectional area of the void space internal to the manifold shell 158. In some preferred versions of the invention, the cross sectional area of the filter structure is at least two times (×2) the cross sectional area of the inside of the manifold in which this structure is seated. This feature of the invention further enhances the pass through area of the filter basket 166. The gap between the shell wall 159 and filter basket lip 196 serves as another path through which liquid and small bits of solid waste can flow through the manifold. This further increases the pass through area internal to the manifold 46.

Collectively the large surface area of the filter structure, the relatively long lengths of the individual gaps of the filter structure and the filter sub-assembly formed by the manifold shell and filter basket lip mean that should sections of some of the gaps clog with solids, a significant fraction of the gaps will remain solid free. Thus, the trapping of solids by the filter basket 166 should not, in many circumstances, appreciably slow the downstream flow of liquids and fine solids through the manifold 46.

From the above description it should be recognized that only a small fraction of the liquid and semisolid waste drawn into mobile unit 30 of this invention is trapped in the manifold 46. Most of the waste flows into the canister 36 or 38. Thus, medical/surgical personnel that occasionally glance at the canister to obtain a rough estimate of the volume of waste drawn from the surgical site will see substantially all the waste so removed. The absence of the small fraction of waste trapped in the manifold does not significantly detract from this accuracy of this estimate.

V. Alternative Embodiments

It should be appreciated that the foregoing is directed to one specific version of the waste collection system of this invention. Other versions of the invention may have features different from what has been described. Thus, there is no requirement that each of the above described features be incorporated in all versions of the invention.

For example, the fact that the waste collection unit 30 is a mobile unit is understood to only be exemplary. In an alternative version of the invention, the waste collection unit is a static unit. The unit may even consist of a receiver connected to a static unit that only has a pump. In this version of the invention, the receiver also connected to a waste collection system (waste plumbing) internal to the hospital; the pump draws the waste into this collection system.

Similarly, there is no requirement that the receiver 44 have a notch or other conduit that allows any uncollected waste to flow out of the receiver.

Further in some versions of the invention, the receiver 44 may be mounted in the canister or other container used to store the collected waste. In these versions of the invention, the valve plate or other valve assembly used to control flow from the receiver, may open directly into the storage space.

Likewise the individual features of this waste collection system may have structures different from what have been described. There is no requirement that in all versions of the invention the manifold opening through which the waste is flowed to the rest of the system also function as the drive member integral with the manifold that receives a feature for actuating the valve integral with the receiver. Similarly, there is no requirement that valve component through which the waste is flowed also serve as the component that is actuated by the manifold.

Thus, in one alternative versions of the invention, the valve element may have an actuating pin. In this version of the invention, the manifold has a keyhole for receiving the pin. This keyhole may be an external slot or a closed end bore. As the manifold is inserted in the receiver, the pin seats against the manifold surfaces defining the slot/bore. Further displacement of the manifold results in the like displacement of the pin and, by extension, the opening and/or closing of the manifold.

In the alternative versions of the invention, the valve integral with the receiver may not be a disk. The valve may be a plate that moves in an arcuate or linear path to open/close the conduit to the downstream components of the system. The valve may not be a planar member. Thus, the valve may be a ball type member that rotates between open and closed positions. In some versions of the invention, a biasing member is provided that normally holds the valve in the closed state. In these versions of the invention, the displacement of the valve drive member by the manifold overcomes the biasing force and displaces the valve into the open state. When the manifold is removed, the biasing member returns the valve to the closed state.

Furthermore, in some versions of the invention, the drive member integral with the manifold that couples to the receiver valve may not be a void-defining feature. In some versions of the invention, the manifold may be formed with a tab or a post. The receiver valve has a drive member with a keyhole or void for receiving the manifold feature. When the manifold is seated in the receiver, the tab/post seats in the keyhole. Further displacement of the manifold results in the actuation of the valve drive member and the resultant opening or closing of the valve.

Likewise, in some versions of the invention the valve has an actuating member separate from the valve itself. This actuating member, upon displacement by the manifold insertion/removal, moves the valve between the open/closed states. Thus, if the valve has a ball- or cylindrically-shaped head, the actuating member may be a drive link that, when longitudinally displaced rotates the valve head.

It should thus be appreciated that, in these alternative versions of the invention, the linear insertion/removal of the manifold may source of the force that causes the opening/closing of the complementary manifold receiver valve.

Also it may be desirable to provide a releasable latch mechanism for holding the valve in a particular state. Thus with the disclosed valve disk 132 it may be desirable to provide spring biased ball-in-detent to prevent unintended rotation of the valve disk. In some versions of the invention the ball is mounted to and rotated with the valve disk. In these versions of the invention receiver adapter face plate 96 is formed with at least one detent for capturing the ball. This assembly keeps the valve disk from rotating from the closed state. Also by preventing rotation of the valve disk 132, the likelihood that the valve boss 136 will not be aligned to seat in manifold opening 170 is essentially eliminated. Alternatively, the ball and spring are mounted in a bore that opens inwardly from the receiver adapter face plate 96. The valve disk is formed with an appropriate detent for receiving the valve.

The manifold may be provided with a drip stop different from what has been disclosed. Thus, the drip stop that selectively blocks flow out of the opening into the mobile unit may be formed with one or three or more lips, flaps or other members that are selectively displaced to open/close the drip stop. One such valve is a duck-billed valve.

In some versions of the invention, the flow-blocking components of the drip stop may not be abutting flaps. A flapper valve that may or may not be spring biased can perform this function. A normally closed umbrella type valve may function as the drip reducing member of the drip stop. In this version of the invention, the valve boss abuts and displaces a valve stem so to force the valve into the open state. A normally-closed spring biased poppet valve may also be used to prevent drip release. In these versions of the invention, as well as the above described version wherein opposed flaps form the valve, the valve is opened as a result of a mechanical force placed on the valve by the receiver. The valve then automatically closes upon the removal of the force imposing valve-associated member.

It should be appreciated that in some alternative drip stops of the invention, the valve component of the drip stop may not further function as the component that prevents leakage around the valve boss. In these versions of the invention, there is separate drip stop component that forms a barrier between the valve boss and the adjacent outlet opening-defining section of the manifold. A grommet may perform this function.

Assemblies other than the disclosed flapper valve unit may be used to prevent fluid flow from the manifold 46 out of fittings 48. Some flapper valves, for example, have a reinforcing member such as domes or ribs disposed on their backsides. These reinforcing members prevent valve collapse in the presence of high back pressures. Duck billed valves mounted in the fittings 48 may perform this check valve function. These include duck bill valves with three or more lips. Again, umbrella valves, poppet valves, spring loaded valve may be fitted to the manifold to reduce the likelihood of leakage through the fittings 48.

Features other than tabs may be integral with the manifold to ensure that the manifold when inserted into the receiver, manifold opening 170 is aligned with the valve disk boss 136 and bore 138. Thus, in an alternative version of the invention, the manifold is formed with one or more slots or other void spaces along the outer surface thereof. These slots receive alignment pins integral with the manifold receiver. In these versions of the invention, the surfaces of the manifold that define these slots may also function as cam surfaces. Thus, as the manifold is inserted in the receiver, the manifold is urged off these static alignment pins further into the receiver.

Likewise, in an alternative versions of the invention, the camming surfaces that, upon manifold rotation, urge the manifold proximally rearward may not be on the manifold receiver. In some versions of the invention, the alignment tabs, grooves or notches integral with the manifold may have angled or tapered profiles. As the manifold is rotated, the abutment of these surfaces against fixed surfaces integral with the receiver, result in the manifold being moved proximally. Further, in some versions of the invention, there is only a single camming surface integral with the receiver and/or manifold.

Also, in some versions of the invention, the manifold may be provided with a data carrier and the complementary receiver has a device capable of reading the store data. Such a manifold is disclosed in the Applicants' Assignee's U.S. Patent App. No. 60/780,474, SURGICAL WASTE COLLECTION SYSTEM WITH FLUID STREAM PRE-FILTER, filed 8 Mar. 2006, published as WO 2007/103842, the contents of which are incorporated herein by reference. As described in the incorporated-by-reference application, the data carrier stores data used to regulate operation of the unit to which the manifold with which the data carrier is integral is attached. These data include: manifold use history; vacuum level; and expiration data. The receiver data reader forwards these data to a processor that regulates actuation of the waste collection unit. Based on these data, the processor: determines whether or not the attached manifold can be used; and regulates the operation of the suction pump.

Further there is no requirement that in all versions of the invention, the filter basket be suspended from the top of the manifold. In some versions of the invention, the filter basket may be suspended from a post that extends upwardly from the bottom of the manifold. Alternatively, the filter basket may be snap fitted into the side wall of the manifold.

Similarly, in some versions of the manifold, it may not be necessary to provide a filter such as the described filter basket. Also, some manifolds of this invention may only be provided with a single fitting 48. An advantage of this structure is that, when only a single suction line 50 is attached to the system 30, one does not have to be concerned with the question of whether or not unused fittings are capped.

Also, alternative versions of the manifold may include an O-ring or other compressible member between the shell 158 and cap 164. This member serves as seal between these two components so as to minimize, if not eliminate, the loss of vacuum.

Further, there is no requirement that the manifold shell fingers 161 and 162 used to align the shell with the cap 164 always be 180° apart from each other. In other versions of the invention, fingers 161 and 162 may be spaced closer together. Thus the complementary pairs of ribs 226 and 228 would likewise be positioned on the cap skirt 220 to be closer together so as to receive, respectively fingers 161 and 162.

Therefore, it is an object of the appended claims to cover all such variations and modifications that come within the true spirit and scope of this invention.

What is claimed is:

1. A method of assembling a manifold for filtering waste liquid being drawn under influence of suction of a medical waste collection system, the manifold including a shell including an open distal end and a proximal end base defining an outlet opening, a cap including a cap skirt and a head at an end of the cap skirt, and a filter element, the method comprising:
   positioning the filter element within the shell;
   fitting basket hands of the filter element between first pairs of ribs of the cap skirt, thereby facilitating rotational alignment of the cap and the filter element;
   fitting fingers of the shell between second pairs of ribs of the cap skirt, thereby facilitating rotational alignment of the cap and the shell; and
   securing the cap to the shell to cover the open distal end of the shell.

2. The method of claim 1, wherein each of the first pairs of ribs are spaced apart by a different distance corresponding to a respective one of the basket hands.

3. The method of claim 1, wherein each of the second pairs of ribs are spaced apart by a different distance corresponding to a respective one of the fingers of the shell.

4. The method of claim 1, wherein the step of securing the cap to the shell further comprises inserting the shell into the cap skirt.

5. The method of claim 4, wherein the step of securing the cap to the shell further comprises compressing an O-ring between the shell and the cap to provide a seal.

6. The method of claim 1, further comprising securing a drip stop to the proximal end base of the shell by resiliently deforming and positioning the drip stop such that upon resilient return a portion of the proximal end base is seated in a slot defined by the drip stop.

7. The method of claim 1, further comprising attaching on the manifold a data carrier storing data used to regulate operation of the medical waste collection system.

8. The method of claim 1, further comprising forming the filter element to include a basket lip having an outer diameter less than an inner diameter of the shell to define a gap sized as a flow through path through which liquid and small bits of matter are configured to pass to prevent clogging of downline components.

9. The method of claim 1, wherein the manifold further includes a flapper valve unit including a hub and flapper valves, wherein the method further comprises securing the flapper valve unit to the head of the cap by fitting ears through holes defined by a hub of the flapper valve unit and cap holes defined by the cap, wherein the ears are configured to snap lock to the head of the cap.

10. The method of claim 9, wherein the hub of the flapper valve unit is compressed with the ears snap locked to the head of the cap.

11. The method of claim 9, further comprising positioning flapper valves of the flapper valve unit to be seated over ports of the cap, wherein a square-in-square engagement between the ears and the cap holes of the cap prevents rotation of the filter element during assembly.

12. The method of claim 1, further comprising securing the filter element to the cap.

13. A method of assembling a manifold for filtering waste liquid being drawn under influence of suction of a medical waste collection system, the manifold including a shell including an open distal end and a proximal end base defining an outlet opening, a cap including a cap skirt and a head at an end of the cap skirt, and a filter element, the method comprising:
   positioning the filter element within the shell;
   fitting basket hands of the filter element between first pairs of ribs of the cap skirt, thereby facilitating rotational alignment of the cap and the filter element;
   fitting fingers of the shell between second pairs of ribs of the cap skirt, thereby facilitating rotational alignment of the cap and the shell; and
   inserting the shell into the cap skirt so that a lip of the shell is seated on a step of the cap skirt to secure the cap to the shell and cover the open distal end of the shell.

14. The method of claim 13, wherein the step of securing the cap to the shell further comprises compressing an O-ring between the shell and the cap to provide a seal.

15. The method of claim 13, wherein each of the first pairs of ribs are spaced apart by a different distance corresponding to a respective one of the fingers of the shell.

16. The method of claim 13, further comprising attaching on the manifold a data carrier storing data used to regulate operation of the medical waste collection system.

* * * * *